United States Patent
Willis

(10) Patent No.: US 11,191,478 B2
(45) Date of Patent: Dec. 7, 2021

(54) METHODS FOR PREVENTING AND TREATING MOTOR RELATED NEUROLOGICAL CONDITIONS

(71) Applicant: PhotoPharmics, Inc., American Fork, UT (US)

(72) Inventor: Gregory Lynn Willis, Woodend (AU)

(73) Assignee: PhotoPharmics, Inc., American Fork, UT (US)

( * ) Notice: Subject to any disclaimer, the term of this patent is extended or adjusted under 35 U.S.C. 154(b) by 104 days.

(21) Appl. No.: 14/094,510

(22) Filed: Dec. 2, 2013

(65) Prior Publication Data

US 2014/0128745 A1 May 8, 2014

Related U.S. Application Data

(63) Continuation of application No. PCT/IB2012/002553, filed on Feb. 12, 2012, which is a continuation-in-part of application No. PCT/IB2012/001161, filed on May 31, 2012.
(Continued)

(51) Int. Cl.
*A61B 5/00* (2006.01)
*A61N 5/06* (2006.01)
(Continued)

(52) U.S. Cl.
CPC .......... *A61B 5/4836* (2013.01); *A61B 5/0082* (2013.01); *A61B 5/4082* (2013.01);
(Continued)

(58) Field of Classification Search
CPC . A61B 5/1124; A61B 5/4836; A61B 5/45839; A61B 5/162; A61B 5/4082;
(Continued)

(56) References Cited

U.S. PATENT DOCUMENTS 5,274,403 A * 12/1993 Gott ................. G02C 7/104
351/159.63
5,767,162 A 6/1998 Weber et al.
(Continued)

FOREIGN PATENT DOCUMENTS

CN 102056625 A 5/2011
JP 2001-503394 A 3/2001
(Continued)

OTHER PUBLICATIONS

Gasio et al, "Dawn-dusk simulation light therapy of disturbed circadian rest-activity cycles in demented elderly", Experimental Gerontology 38 (2003) 207-216.*
(Continued)

*Primary Examiner* — Oommen Jacob
(74) *Attorney, Agent, or Firm* — Dentons Durham Jones Pinegar

(57) ABSTRACT

Methods for preventing or treating motor-related neurological conditions include using ocular light therapy in connection with a conventional therapy for a motor-related neurological condition, such as a drug regimen, to adjust levels of melatonin and/or dopamine in the body of a subject. The ocular light therapy may include elevated levels of blue-green light or green light (e.g., light within a wavelength range of 460 nm to 570 nm, 490 nm to 570 nm, about 520 nm to 570 nm, etc.). The ocular light therapy may also include reduced levels of amber, orange and/or red light. Methods for diagnosing motor-related neurological conditions include ocular administration of increased amounts of amber, orange and/or red light to cause a subject to temporarily exhibit one or more symptoms of any motor-related neurological condition to which the subject is predisposed, or which the subject may already be experiencing.

41 Claims, 13 Drawing Sheets

The Effect of Strategic Photo-Pharmacotherapy on Tremor (A) and Micrographia (B) in a *de novo* PD Patient

Related U.S. Application Data

(60) Provisional application No. 61/491,860, filed on May 31, 2011.

(51) Int. Cl.
    *A61M 21/00*     (2006.01)
    *A61B 5/11*     (2006.01)
    *A61B 5/16*     (2006.01)
    *G06K 9/00*     (2006.01)

(52) U.S. Cl.
    CPC .......... *A61B 5/4839* (2013.01); *A61M 21/00* (2013.01); *A61N 5/0618* (2013.01); *A61N 5/0622* (2013.01); *A61B 5/1124* (2013.01); *A61B 5/162* (2013.01); *A61M 2021/0044* (2013.01); *A61M 2021/0077* (2013.01); *A61N 2005/0663* (2013.01); *G06K 9/00161* (2013.01)

(58) Field of Classification Search
    CPC ............ A61B 5/4839; A61B 5/0082; A61M 2021/0044; A61M 2021/0005; A61M 2021/0077; A61M 21/00; G06K 9/00161; A61N 2005/0663; A61N 5/0618; A61N 5/0622
    USPC ................................................. 600/476, 407
    See application file for complete search history.

(56) References Cited

U.S. PATENT DOCUMENTS

| | | | |
|---|---|---|---|
| 6,310,085 B1* | 10/2001 | Willis | A61K 31/165 514/415 |
| 6,615,409 B2* | 9/2003 | Youmans | A61F 9/028 2/432 |
| 6,875,225 B1 | 4/2005 | Pederson et al. | |
| 7,147,319 B2* | 12/2006 | Lin | A61M 21/00 351/51 |
| 7,232,456 B2* | 6/2007 | Chernoff | A61N 5/0616 607/89 |
| 7,520,607 B2* | 4/2009 | Casper | G02C 7/10 351/159.65 |
| 7,678,140 B2 | 3/2010 | Brainard et al. | |
| 7,984,989 B2* | 7/2011 | Gruber | G02C 7/108 351/159.59 |
| 8,104,481 B2 | 1/2012 | Pederson et al. | |
| 8,366,755 B2 | 2/2013 | Brainard et al. | |
| 8,453,651 B2 | 6/2013 | Pederson et al. | |
| 8,721,698 B2 | 5/2014 | Pederson et al. | |
| 9,844,116 B2* | 12/2017 | Soler | H05B 45/10 |
| 9,889,314 B2* | 2/2018 | Kim | A61N 5/0618 |
| 9,943,700 B2 | 4/2018 | Pederson et al. | |
| 10,007,039 B2* | 6/2018 | Aube | B60J 3/007 |
| 10,213,619 B2* | 2/2019 | Brainard | A61N 5/06 |
| 10,603,507 B2 | 3/2020 | Brainard et al. | |
| 2002/0068692 A1 | 6/2002 | Willis | |
| 2003/0109799 A1* | 6/2003 | Brown | 600/558 |
| 2003/0229107 A1* | 12/2003 | Cowan | A61B 5/055 514/263.33 |
| 2004/0049247 A1 | 3/2004 | Perricone | |
| 2004/0225339 A1* | 11/2004 | Yaroslavsky | A61N 5/062 607/88 |
| 2004/0225340 A1* | 11/2004 | Evans | A61M 21/00 607/88 |
| 2005/0020664 A1 | 1/2005 | Zisapel et al. | |
| 2005/0024853 A1* | 2/2005 | Thomas-Benedict | A61N 5/0619 362/103 |
| 2006/0007390 A1* | 1/2006 | Lin | A61M 21/00 351/158 |
| 2006/0009822 A1* | 1/2006 | Savage | A61M 21/00 607/88 |
| 2006/0217783 A1* | 9/2006 | Harold | A61N 1/36046 607/53 |
| 2006/0258896 A1 | 11/2006 | Haber et al. | |
| 2007/0049576 A1 | 3/2007 | Barlow et al. | |
| 2008/0015660 A1* | 1/2008 | Herekar | A61N 5/062 607/88 |
| 2008/0051858 A1 | 2/2008 | Haber et al. | |
| 2008/0103561 A1 | 5/2008 | Moscovici | |
| 2008/0131492 A1* | 6/2008 | Nangia | A61K 9/2072 424/449 |
| 2008/0266690 A1* | 10/2008 | Toda | A61N 5/0618 359/885 |
| 2009/0281604 A1* | 11/2009 | De Boer | H05B 31/50 607/88 |
| 2010/0149483 A1* | 6/2010 | Chiavetta, III | G02B 5/289 351/159.63 |
| 2010/0179469 A1* | 7/2010 | Hammond et al. | 604/20 |
| 2010/0189698 A1 | 7/2010 | Willis | |
| 2010/0262211 A1* | 10/2010 | Glaubitt | C03C 17/006 607/88 |
| 2011/0202114 A1* | 8/2011 | Kessel | A61F 9/008 607/88 |
| 2011/0262656 A1* | 10/2011 | Nagae | C23C 14/10 427/535 |
| 2012/0008326 A1* | 1/2012 | Jou | A61M 21/02 362/293 |
| 2012/0172419 A1* | 7/2012 | Neitz | C12N 15/85 514/44 R |
| 2012/0215290 A1* | 8/2012 | Chen | 607/90 |
| 2012/0300447 A1* | 11/2012 | Maxik | F21K 9/23 362/230 |
| 2014/0046409 A1* | 2/2014 | Kang | A61N 5/0616 607/89 |
| 2014/0128745 A1* | 5/2014 | Willis | A61B 5/4836 600/476 |

FOREIGN PATENT DOCUMENTS

| | | | |
|---|---|---|---|
| JP | 2009112804 A | 5/2009 | |
| JP | 2010-526645 A | 8/2010 | |
| KR | 2001-0112372 A | 12/2001 | |
| KR | 2010-0040894 A | 4/2010 | |
| WO | 1998/015267 A1 | 4/1998 | |
| WO | 2000059504 A1 | 10/2000 | |
| WO | 2006098719 A1 | 9/2006 | |
| WO | 2008/141296 A1 | 11/2008 | |
| WO | WO 2009003226 A1 * | 1/2009 | |
| WO | WO-2009003226 A1 * | 1/2009 | ........... A61K 9/0048 |
| WO | 2009124189 A1 | 10/2009 | |
| WO | 2009003226 A1 | 9/2010 | |
| WO | 2010078581 A1 | 6/2012 | |
| WO | 2012164393 A1 | 12/2012 | |

OTHER PUBLICATIONS

Wright et al., Effect of Light Wavelength on Suppression and Phase Delay of the Melatonin Rhythm, Chronobiology International, 18(5), 801-808 (2001).*

Sartucci et al, "Visual-evoked potentials to onset of chromatic red-green and blue-yellow gratings in Parkinson's disease never treated with L-dopa.", J Clin Neurophysiol. Oct. 2006;23(5):431-5.*

Bliwise et al ("Disruptive Nocturnal Behavior in Parkinson's Disease and Alzheimer's Disease", Journal of Geriatric Psychiatry and Neurology, vol. 8 , Apr. 1995) teaches sundowning is a commonly encountered clinical problem in most forms of dementia and causes disruptive nocturnal behavior in patients with Alzheimer's disease and Parkinson's disea.*

Oren, D. A. "Retinal melatonin and dopamine in seasonal affective disorder" J Neural Transm [GenSect] (1991) 83:85-95.*

Sartucci et al. "Visual-Evoked Potentials to Onset of Chromatic Red-Green and Blue-Yellow Gratings in Parkinson's Disease Never Treated With L-Dopa", J Clin Neurophysiol. Oct. 2006; 23(5): 431-435.*

(56) References Cited

OTHER PUBLICATIONS

Wright et al., Effect of Light Wavelength on Suppression and Phase Delay of the Melatonin Rhythm, Chronobiology International, 18(5), 801-808 (2001), (Year: 2001).*
Willis et al. Primary and secondary features of Parkinson's disease improve with strategic exposure to bright light: a case series study. Chronobiology International, 24(3): 521-537, (2007) (Year: 2007).*
Wright ["Effect Of Lightwavelength On Suppression And Phase Delay Of The Melatonin Rhythm" Chronobiology International, 18(5), 801-808 (2001)] (Year: 2001).*
Anderson [ "Lux vs. wavelength in light treatment of Seasonal Affective Disorder"Acta Psychiatr Scand 2009: 120: 203-212]. (Year: 2009).*
Gooley ["Spectral Responses of the Human Circadian System Depend on the Irradiance and Duration of Exposure to Light", www.ScienceTranslationalMedicine.org, May 12, 2010 vol. 2 Issue 31] (Year: 2010).*
Figuero [Retinal mechanisms determine the subadditive response to polychromatic light by the human circadian system, Neuroscience Letters 438 (2008) 242-245], (Year: 2008).*
Paus [Bright Light Therapy in, Parkinson's Disease: A Pilot Study, "Movement Disorders, vol. 22, No. 10, 2007"], (Year: 2007).*
Revell [Light-Induced Melatonin Suppression In Humans with Polychromatic And Monochromatic Light, Chronobiology International, 24(6): 1125-1137, (2007)]. (Year: 2007).*
Australian Patent Office Acting as the International Searching Authority, "International Search Report and Written Opinion," dated Oct. 15, 2012, in corresponding PCT application No. PCT/IB2012/001161.
Australian Patent Office Acting as the International Searching Authority, "International Search Report and Written Opinion," dated May 13, 2013, in corresponding PCT application No. PCT/IB2012/002553.
Gregory L. Willis et al., "Primary and secondary features of Parkinson's Disease improve with strategic exposure to bright light: A case series study," Chronobiology International, vol. 24, No. 3, 2007, pp. 521-537.
Helen R. Wright et al., "Effect of light wavelength on suppression and phase delay of the melatonin rhythm," Chronobiology International, vol. 18, No. 5, 2001, pp. 801-808.
Gregory L. Willis, "Parkinson's Disease as a neuroendocrine disorder of circadian function: Dopamine-Melatonin imbalance and the visual system in the genesis and progression of the degenerative process," Reviews in the Neurosciences, vol. 19, 2008, pp. 245-316.
Terman, M., "Evolving Applications of Light Therapy," Sleep Medical Reviews 11:497-507 (2007).
Australian Government, IP Australia, "Patent Examination Report No. 1," dated Aug. 14, 2014 in Australian patent application No. 2012264320.
Australian Government, IP Australia, "Patent Examination Report No. 2," dated Jul. 17, 2015 in Australian patent application No. 2012264320.
Australian Government, IP Australia, "Patent Examination Report No. 1," dated Nov. 16, 2016 in Australian patent application No. 2015215840.
Australian Government, IP Australia, "Examination Report No. 2," dated Nov. 16, 2017 in Australian patent application No. 2015215840.
Canadian Intellectual Property Office, "Examiner's Report," dated Dec. 18, 2017 in Canadian patent application No. 2,837,823.
State Intellectual Property Office of the People's Republic of China, "Notification of the First Office Action," dated Jul. 1, 2015 in Chinese patent application No. 201280034058.7.
State Intellectual Property Office of the People's Republic of China, "Notification of the Second Office Action" dated May 27, 2016 in Chinese patent application No. 201280034058.7.
State Intellectual Property Office of the People's Republic of China, "Notification of the Third Office Action" dated Jan. 25, 2017 in Chinese patent application No. 201280034058.7.
European Patent Office, "Extended European Search Report," dated Dec. 1, 2014 in European patent application No. 12792581.6.
Japanese Patent Office, "Notification of Reasons for Rejection" and "Record of Prior Art Search Results," dated May 17, 2016 in Japanese patent application No. 2014-513269.
Japanese Patent Office, "Notification of Reasons for Rejection," dated Nov. 28, 2016 in Japanese patent application No. 2014-513269.
Japanese Patent Office, "Final Rejection," dated May 18, 2017 in Japanese patent application No. 2014-513269.
IP Australia, "Examination Report," Australian Patent Application No. 2017261574, dated Jan. 14, 2019, 5 pages.
IP Australia, "Examination Report," Australian Patent Application No. 2017265164, dated Feb. 5, 2019, 6 pages.
Canadian Intellectual Property Office, "Examiner's Report," Canadian Patent Application No. 2837993, dated Jan. 18, 2018, 4 pages.
Japanese Patent Office, "First Office Action Appeal Board," Japanese Patent Application No. 2014513269, dated Sep. 18, 2018, 22 pages.
Japanese Patent Office, "Notice of Refusal," Japanese Patent Application No. 2014513269, dated May 17, 2016, 7 pages.
Willis, G.L., "Parkinson's disease as a neuroendocrine disorder of circadian function: dopamine-melatonin imbalance and the visual system in the genesis and progression of the degenerative process," Reviews in the Neurosciences, 19:245-316, (2008) 72 pages.
Korean Intellectual Property Office, "Notice of Refusal," Korean Patent Application No. 2013-7035022, dated Nov. 21, 2018, 13 pages.
Canadian Intellectual Property Office, "Examiner's Report," Canadian patent application No. 2837823, dated Nov. 20, 2018.
Canadian Intellectual Property Office, "Examiner's Report," Canadian Patent Application No. 2837823, dated Jan. 24, 2020.
Korean Intellectual Property Office, "Notification of Reason(s) for Rejection," Korean Patent Application 10-2019-7039008, dated Feb. 28, 2020.
Japan Patent Office, "Notification of Reasons For Rejection," Japanese Patent Application 2019-026571, dated Feb. 27, 2020.
Japan Patent Office, "Notification of Final Rejection," for Japanese Patent Application 2019-026571, dated Dec. 21, 2020.
Critchley, PH, et al., "Fatigue and melatonin in Parkinson's disease," J Neurol Neurosurg Psychiatry 54:91 (1991).
Fertl, E, et al., "Circadian secretion pattern of melatonin in Parkinson's disease," J Neural Transm Park Dis Dement Sect 1991; 3:41-7 (1991).
Sandyk, R, "The Accelerated Aging Hypothesis of Parkinson's Disease is not Supported by the Experimental Models ol Schizophrenia," Int'l J Neurosci 90:271-5 (1997).
Bordet, R, et al. "Study of circadian melatonin secretion pattern at different stages of Parkinson's disease," Clin Neuropharmacol 26.2: 65-72 (2003).
Kay, SR, et al., "Experimental models of schizophrenia," Int'l J Neurosci 58:69-82 (1991).
Sandyk, R, "The association of pineal calcification with drug-induced dystonic movements," Int'l J Neurosci 53:217-22 (1990).
Tamtaji, OR, et al. "Melatonin and Parkinson Disease: Current Status and Future Perspectives for Molecular Mechanisms," Cell Mol Neurobiol 40(1):15-23 (2020) doi: 10.1007/s10571-019-00720-5. Epub Aug. 6, 2019. PMID 31388798.
Cardinali, DP, "Melatonin: Clinical Perspectives in Neurodegeneration," Front Endocrinol (Lausanne) 10:480 (Jul. 16, 2019).
Reiter, et al. "Oxidative toxicity in models of neurodegeneration: responses to melatonin." Restorative Neurol and Neurosci 12.2, 3: 135-142 (1998).
Tapias, V, et al., "Melatonin treatment potentiates neurodegeneration in a rat rotenone Parkinson's disease model," J Neurosci Res 88(2):420-7 (2010).
Antolín, I, et al. "Protective effect of melatonin in a chronic experimental model of Parkinson's disease." Brain Res 943.2: 163-173 (2002).
Mayo, JC, et al. "Melatonin prevents apoptosis induced by 6-hydroxydopamine in neuronal cells: implications for Parkinson's disease." J Pineal Res 24.3: 179-192 (1998).
Dabbeni-Sala, F, et al. "Melatonin protects against 6-OHDA-induced neurotoxicity in rats: a role for mitochondrial complex I activity," FASEB J 15.1:164-170 (2001).

(56) References Cited

OTHER PUBLICATIONS

Johnson, S, "Micronutrient accumulation and depletion in schizophrenia, epilepsy, autism and Parkinson's disease?" Med Hypoth 56:641-5 (2001).
Sandyk, R, "Pineal melatonin functions: possible relevance to Parkinson's disease," Int'l J Neurosci 50:37-54 (1990).
Sandyk, R, "Pineal melatonin functions and the depression of Parkinson's disease: A hypothesis," Int'l J Neurosci 51:73-7 (1990).
Sandyk, R, "Accelerated growth of malignant melanoma by levodopa in Parkinson's disease and role of the pineal gland," Int'l J Neurosci 63:137-40 (1992).
Canadian Intellectual Property Office, "Examiner's Report," Canadian Application No. 2837823, dated Mar. 11, 2021.
European Patent Office, "Communication pursuant to Article 94(3) EPC," European Application No. 12792581.6, dated Mar. 18, 2021.
Korean Intellectual Property Office, "Notification of Reasons for Rejection," Korean Patent Application 10-2020-7034509, dated Mar. 8, 2021.
Japan Patent Office, "Office Action," Japanese Patent Application No. 2014-513269, dated Mar. 19, 2019, 8 pages.
Figueiro, MG, et al., "Circadian effectiveness of two polychromatic lights in suppressing human nocturnal melatonin," Neurosci Lett 406:293-297 (2006).
Figueiro, MG, et al., "Demonstration of additivity failure in human circadian phototransduction," Neuroendocrinol Lett 26(5):493-98 (Oct. 2005).
Schnapf, JL, et al., "Spectral sensitivity of human cone receptors," Nature, 433(7027)749-54 (Feb. 17, 2005).

\* cited by examiner

METHODS FOR PREVENTING AND TREATING MOTOR RELATED NEUROLOGICAL CONDITIONS

CROSS-REFERENCE TO RELATED APPLICATIONS

This application is a continuation of international patent application no. PCT/IB2012/002553, filed on Dec. 2, 2012 and titled "METHODS FOR PREVENTING AND TREATING MOTOR-RELATED NEUROLOGICAL CONDITIONS ("the '553 PCT Application"), which is a continuation-in-part of international patent application no. PCT/IB2012/001161, filed on May 31, 2012 and titled "METHODS FOR PREVENTING AND TREATING MOTOR-RELATED NEUROLOGICAL CONDITIONS" ("the '161 PCT Application"). This application is also a continuation-in-part of the '161 PCT Application, which claims priority to U.S. Provisional Patent Application No. 61/491,860, filed on May 31, 2011 and titled "METHODS FOR PREVENTING AND TREATING MOTOR-RELATED NEUROLOGICAL CONDITIONS" ("the '860 Provisional Application"). The entire disclosure of each of the '553 PCT Application, the '161 PCT Application and the '860 Provisional Application is, by this reference, incorporated herein.

TECHNICAL FIELD

The present invention relates generally to methods for preventing or treating motor-related neurological conditions and, more specifically, to methods that include stimulating a dopaminergic response by the body of a subject, which may include adjusting levels of one or more of monoamines, such as melatonin, dopamine and serotonin and/or their analogs or derivatives within the body of a subject to reduce or eliminate primary and/or secondary symptoms of a motor-related neurological condition, or to prevent or treat a motor-related neurological condition. In particular embodiments, the present invention relates to the use of light therapy in combination with one or more traditional therapies for adjusting levels of melatonin and/or melatonin analogs and/or levels of dopamine and/or dopamine derivatives in a manner that reduces or eliminates symptoms of a motor-related neurological condition, halts the progression of a degenerative neurological disease, or prevents or treats a motor-related neurological condition. In embodiments of the present invention, light therapy may be used in conjunction with drug therapy for addressing motor-related neurological conditions.

BACKGROUND OF RELATED ART

Motor-related neurological conditions, which are also referred to as "movement disorders," and other neuropsychiatric disorders typically result from the degeneration of neurons in the central nervous system. As neurons degenerate, their ability to convey or otherwise utilize neurotransmitters may diminish, a phenomenon known in the art as "decreased amine function." In particular, in subjects that suffer from Parkinson's disease and many other motor-related neurological conditions, the degeneration of neurons of the so-called "nigro-striatal dopamine" (NSD) system results in a decrease in the ability of these neurons to transmit dopamine, decreasing the ability of neurons of the NSD system to communicate with adjacent neurons. This disruption in communication results in loss of motor control, which is typically progressive and permanent.

Efforts to counteract the loss of motor control include the administration of dopamine precursors, dopamine analogs and enzyme-modifying drugs (e.g., L-dopa, etc.), which act like dopamine without decreasing the natural production of dopamine. By providing the remaining functional neurons of the NSD system with dopamine analogs, the rate at which these neurons can communicate may increase, which may artificially restore at least some of the lost motor control experienced by subjects that suffer from motor-related neurological conditions.

SUMMARY

The present invention includes methods for reducing or eliminating symptoms of motor-related neurological conditions, or for preventing or treating motor-related neurological conditions. Methods that incorporate teachings of the present invention may be useful in conjunction with traditional therapies (e.g., the administration of drugs, etc.), and may reduce the extent of traditional therapies (e.g., the dosages of drugs, etc.) that are needed to address motor-related neurological conditions "Motor-related neurological conditions," as used herein, includes both primary motor-related neurological conditions, as well as secondary conditions, or symptoms, that may accompany or result from a primary motor-related neurological condition. The terms "address" and "addressing," when used in connection with "motor-related neurological conditions," refer to reducing or eliminating symptoms of a motor-related neurological condition, as well as prevention and treatment of the motor-related neurological condition itself.

In various embodiments, a method according to the present invention may include addressing a motor-related neurological condition by stimulating a dopaminergic response by a subject's body and/or adjusting levels of one or more monoamines, such as melatonin, dopamine, serotonin, and their analogs and/or derivatives, within the subject's body. For the sake of simplicity, the term "melatonin," as used herein, includes melatonin and analogs of melatonin, while the term "dopamine" includes dopamine and dopamine analogs, derivatives and other dopamine substitutes and the term "serotonin" includes serotonin and derivatives and analogs thereof. In some embodiments, a method according to the present invention includes addressing (e.g., adjusting, etc.) levels of one or more of melatonin, serotonin and dopamine in a subject's body.

Amounts or levels of one or more monoamines (e.g., melatonin, serotonin and/or dopamine, etc.) within the body of a subject may be adjusted in a manner that addresses a motor-related neurological condition. The term "adjustment," as used herein, includes adjusting levels of monoamines in the body of a subject. The adjustment of one or both of melatonin and dopamine levels in the body of a subject is also referred to herein as "melatonin-dopamine adjustment." Melatonin-dopamine adjustment within the body of a subject may be achieved by regulating production of melatonin. As used herein, "regulating" and similar terms include, but are not limited to, reducing melatonin levels and/or levels of dopamine, as well as moderating levels of melatonin and/or dopamine to adjust a subject's melatonin-dopamine profile.

A dopaminergic response may be stimulated in a variety of ways, such as by administering light to the eyes of a subject, a practice that is also referred to as "ocular light therapy." In various embodiments, ocular light therapy may include the administration of light including, consisting essentially of, or consisting of blue-green light and/or green light (e.g., light within a wavelength range of 460 nm to 570 nm, 490 nm to 570 nm, about 520 nm to 570 nm, about 555 nm, etc.) to the subject. In some embodiments, above-ambient levels (e.g., irradiance, or energy; photon density; intensity; etc.) of blue-green and/or green light may be provided to the subject's eyes. An example of an effective technique for stimulating a dopaminergic response in a subject includes administering ocular light therapy that includes above-ambient amounts of wavelengths of 520 nm to 570 nm and that lacks ambient or above-ambient amounts of other wavelengths of visible light to the subject.

In some embodiments, levels of amber, orange and/or red wavelengths of light (e.g., visible light having wavelengths of greater than 570 nm, visible light having wavelengths of greater than 570 nm to about 750 nm, etc.) administered to a subject may be less than the levels of blue-green and/or green wavelengths in the administered light. In other embodiments, the levels (e.g., irradiance, or energy; photon density; intensity; etc.) of blue-green and/or green light administered to a subject may exceed the corresponding levels of amber, orange and/or red light administered to the subject. In some embodiments, the levels of amber, orange and/or red light administered to a subject may be at most about half the levels of blue, blue-green and/or green light that are administered to the subject. Alternatively, or in addition, levels of one or more of amber, orange and red wavelengths of light may simulate or fall below the levels of amber, orange and/or red wavelengths of light that are present in standard indoor lighting, or the "ambient" densities of one or more of amber, orange and/or red wavelengths of light for any particular narrow band isolated intensity present in ambient light to which a subject is normally exposed, etc.).

By administering ocular light therapy in accordance with one or more of the teachings above, monitoring a subject's condition and response to ocular light therapy, and adjusting one or both of the ocular light therapy and drug therapy administered to the subject, the subject's dopaminergic response may be stimulated, which may vary monoamine (e.g., melatonin, dopamine and/or serotonin, etc.) levels in the body of the subject, in a manner that addresses a motor-related neurological condition. In some embodiments, such administration, monitoring and adjustment may include a reduction in traditional therapies (e.g., the dosages of drugs, such as dopamine derivatives and/or drugs for addressing the side-effects of dopamine derivatives, etc.) that have been used to address the motor-related neurological condition. In some embodiments, the amounts of one or more monoamines in the subject's body or produced by the subject at one or more particular times during the day may be adjusted. In other embodiments, the amounts of one or more monoamines present within the subject's body or produced by the subject throughout the day, or one or more parts of the subject's monoamine profile, may be antagonized, moderated or manipulated. In a more particular embodiment, one or more parts of the subject's monoamine profile may be antagonized, moderated or manipulated to resemble a "normal" monoamine profile; e.g., the monoamine profile of a healthy subject, of a subject that does not suffer from a motor-related neurological condition, or the subject's monoamine profile during an earlier time of day. Moderation of a subject's monoamine profile may include administration of dopaminergic stimulation therapies or monoamine regulation therapies (e.g., light therapy, etc.) at one or more times each day.

In one aspect, the present invention includes, consists essentially of or even consists of the use of light therapy methods for preventing or treating at least one motor-related neurological condition. Examples of such conditions include, but are not limited to, Huntington's chorea, periodic limb movement syndrome, restless leg syndrome, nocturnal myoclonus, Tourette's syndrome, Sundowner's syndrome, REM Sleep Behavior Disorder, schizophrenia, Pick's disease, Punch drunk syndrome, progressive subnuclear palsy, multiple systems atrophy, corticobasilar degeneration, vascular Parkinsonism, Lewy body dementias, diffuse Lewy body disease, Parkinson's plus syndrome, Korsakow's (Korsakoff's) syndrome, multiple sclerosis, medication-induced motor disorders, drug-induced Parkinson's disease, neuroleptics-induced Parkinson's disease, acute dystonia, stroke-post ischemic Parkinsonism, trans-ischemic attack, akathesia dyskinaesia and tardive dyskinaesia. Disorders characterized by features that typify those expressed as secondary symptoms in Parkinson's disease patients and other diseases in which dopamine, serotonin or noradrenaline function is altered may also be treated in accordance with teachings of the present invention. Nonlimiting examples of secondary symptoms include Alzheimer's disease, dementia, depressive pseudo dementia, hydrocephailic dementia, dementia associated with Parkinson's disease, anxiety, generalized anxiety disorder, panic disorder, agoraphobia, obsessive-compulsive disorder, post-traumatic stress disorder, acute stress disorder, depression, bipolar disorder, various personality and insomnia disorders.

In another aspect, the present invention includes the use of light therapy in conjunction with traditional therapies for motor-related neurological conditions. Thus, light therapy may be used in conjunction with drug treatment, cellular (e.g., fetal cell, stem cell, etc.) therapies, surgical treatments and/or other therapies for addressing motor-related neurological conditions. Ocular light therapy may be administered in conjunction with melatonin agonists or antagonists to adjust a subject's melatonin levels.

The present invention also includes systems in which light therapy apparatuses are used in conjunction with traditional therapies.

Use of light therapy to stimulate a dopaminergic response by a subject's body, which may affect monoamine (e.g., melatonin-dopamine, etc.) adjustment in the body of a subject, in conjunction with monitoring of the subject's response to the light therapy, may also enable a physician to reduce a dosage of one or more drugs prescribed for and administered to a subject suffering from a motor-related neurological condition, while, in some instances, having a disease-modifying effect (e.g., slowing or halting progression of the condition, etc.). The course of treatment for a particular subject that suffers from a motor-related neurological condition may be revised to decrease the need for conventional treatment of the motor-related neurological condition (e.g., to decrease the dosage of one more drugs (e.g., a dopamine analog, an analog of another neurotransmitter, etc.), etc., administered to that subject). In some embodiments, when light therapy is used in conjunction with drugs to treat a motor-related neurological condition, a physician may prescribe a lower-than-normal dosage of the drugs (i.e., a lower-than-normal dosage of a drug that is typically required when monoamine production (e.g., melatonin production, etc.) is not regulated). When light therapy is coupled with drug therapy, a physician may define a succinct and strategic controlled therapy package that, in some cases, may be tailored to a particular subject.

In another aspect, the present invention includes standardization among various dopamine replacement therapies and as to how much of any various dopamine replacement therapies any given patient should receive. For example, a daily dosage of 1000 mg of one medication may be the equivalent of a 650 mg daily dosage of another medication. Because the use of light therapy in accordance with teachings of the present invention enables a reduction in dosages of dopamine replacement medication, a drug conversion table may be used to standardize equivalent doses for various dopamine replacement medications. In this way, an effective reduction in the required dosage of a dopamine replacement medication can be achieved regardless of the medicine used. Such a table, titled a "Total Drug Burden" or "TDB" table, is provided in FIG. 22.

The present invention also includes techniques for diagnosing motor-related neurological conditions. In such a technique, increased levels of one or more of amber, orange and red light may be administered to a subject. In some embodiments, the colors and intensities of light administered to the subject may be about the same as or greater than levels of the same color or colors of light present at dusk. The light may be administered ocularly. Administering one or more of amber, orange and red light to the subject may cause the subject to temporarily exhibit symptoms of one or more motor-related neurological conditions before such symptoms would otherwise present themselves. The discovery of such conditions following the administration of amber, orange and/or red light in accordance with teachings of the present invention may enable a physician to make a pre-diagnosis or an early diagnosis of a motor-related neurological condition. In the event that a physician determines that the subject is likely to suffer or will suffer from a motor-related neurological condition, the physician may prescribe a course of treatment for the diagnosed condition. A prescribed course of treatment may include, among other things, use of suitable ocular light therapy, etc., the administration of one or more drugs, and/or other suitable treatments.

Other aspects, as well as features and advantages of various aspects, of the present invention will become apparent to those of ordinary skill in the art through consideration of the ensuing description and the appended claims.

Figure 16:
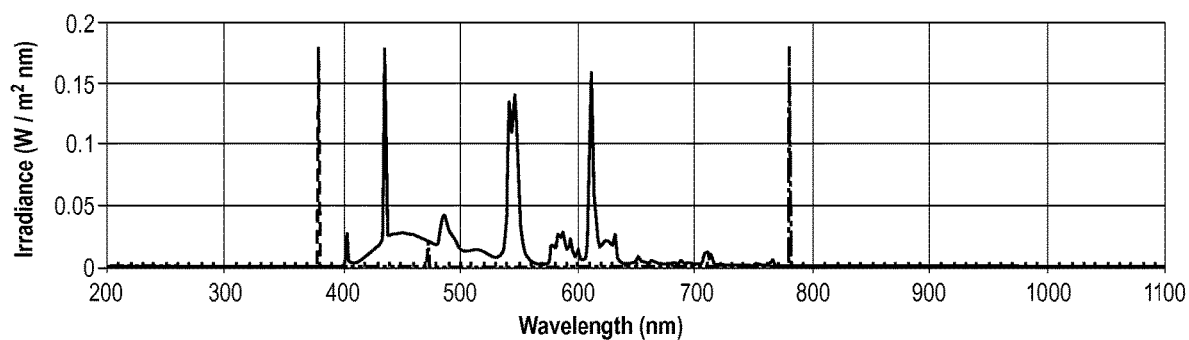
Figure 17:
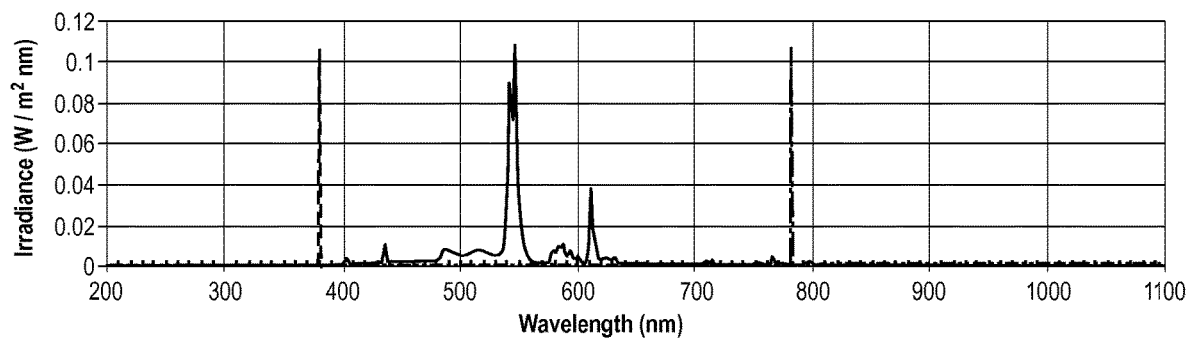
Figure 18:
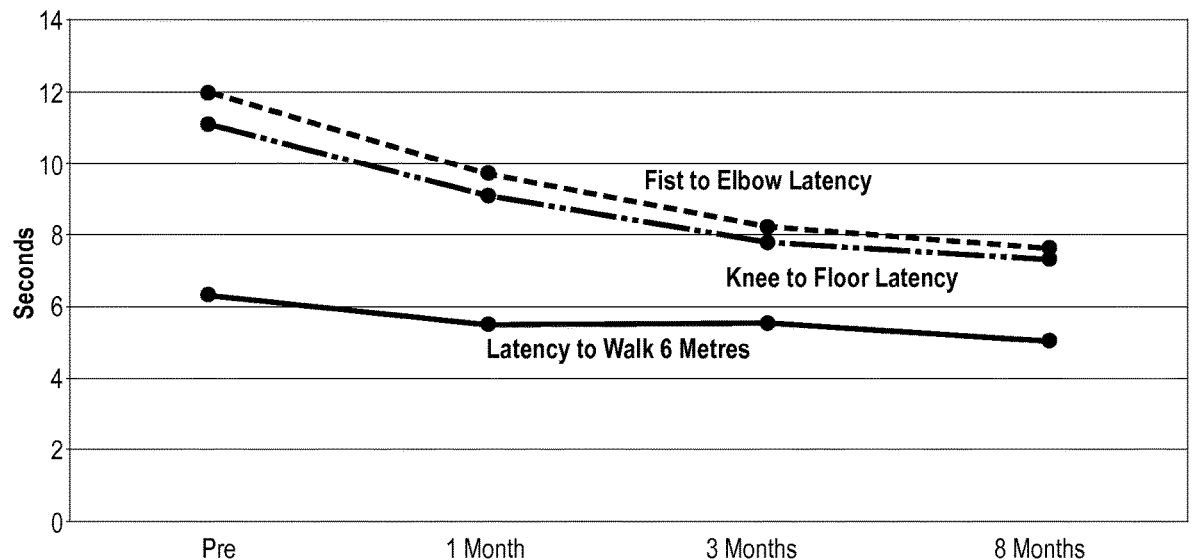
Figure 19:
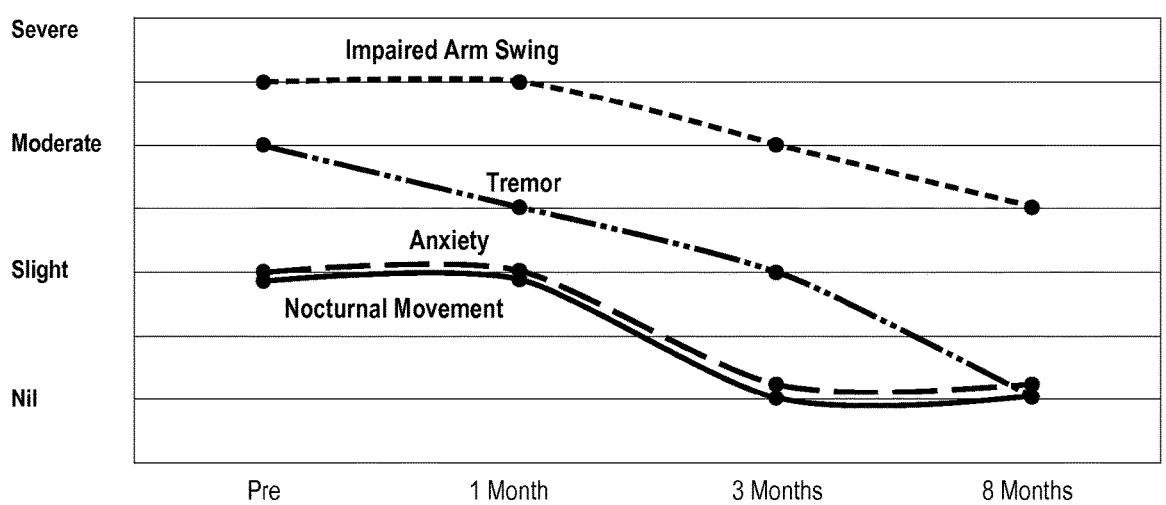
Figure 20:
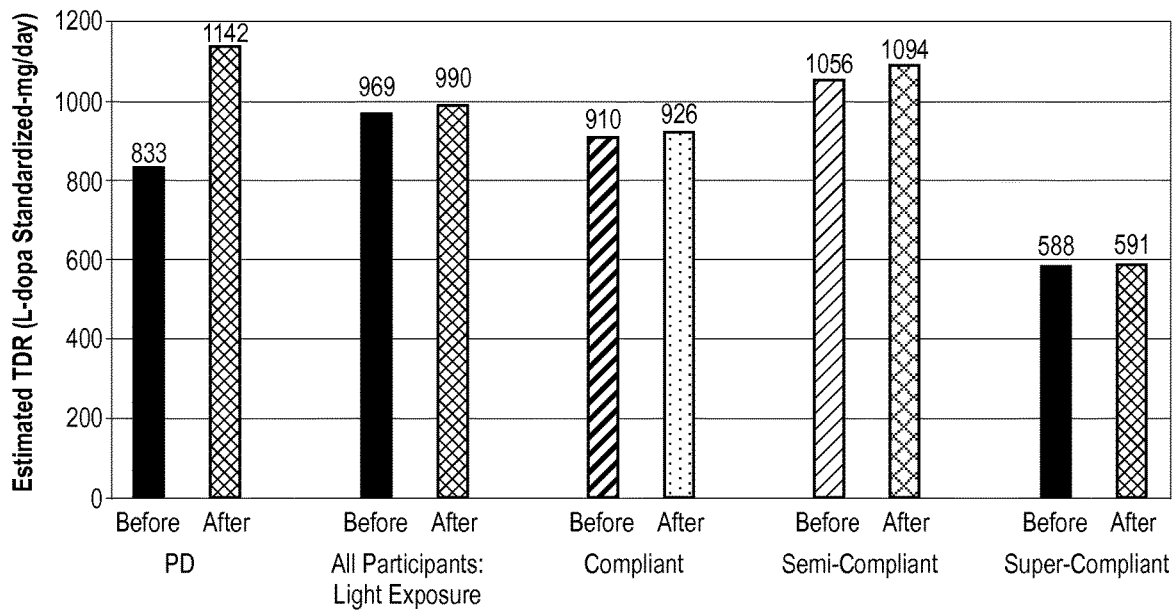
Figure 21:
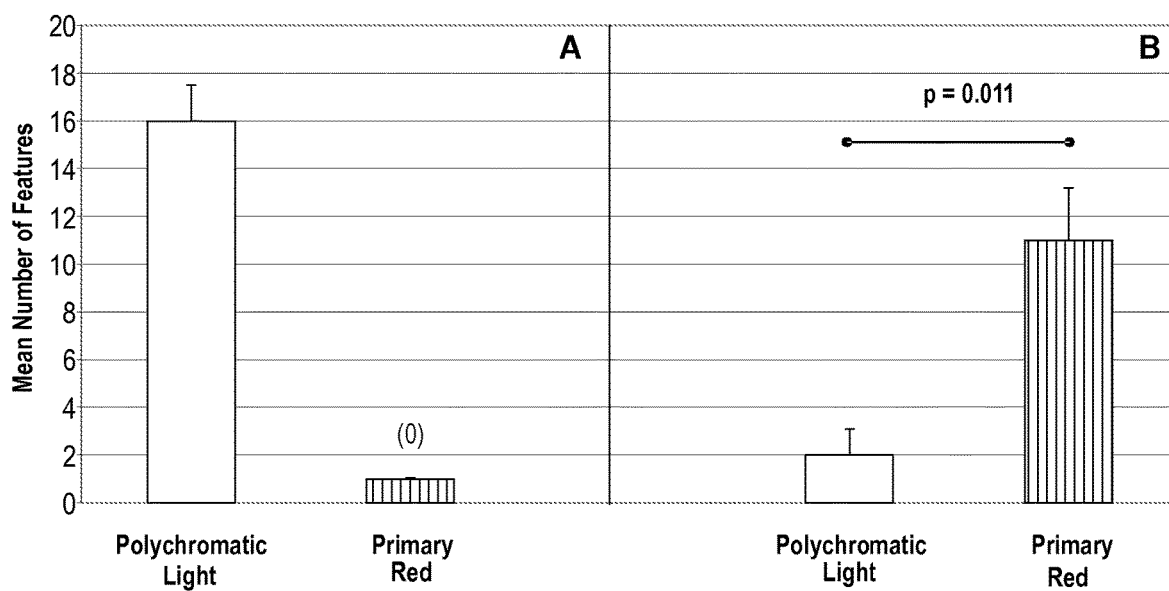
Figure 22:
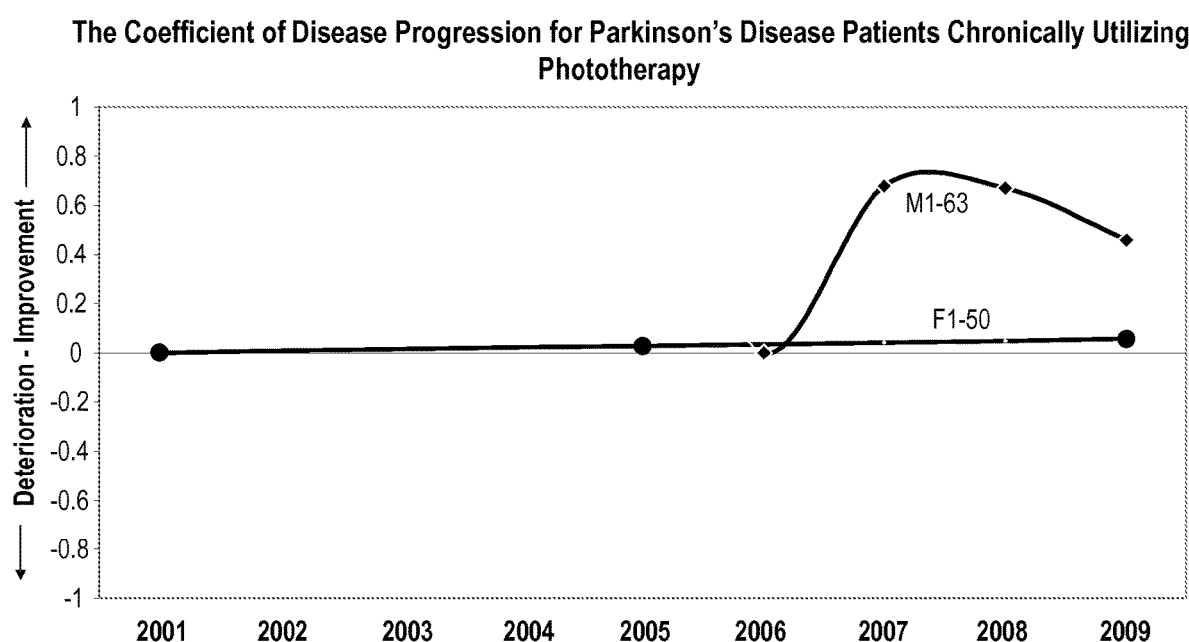
Figure 23:
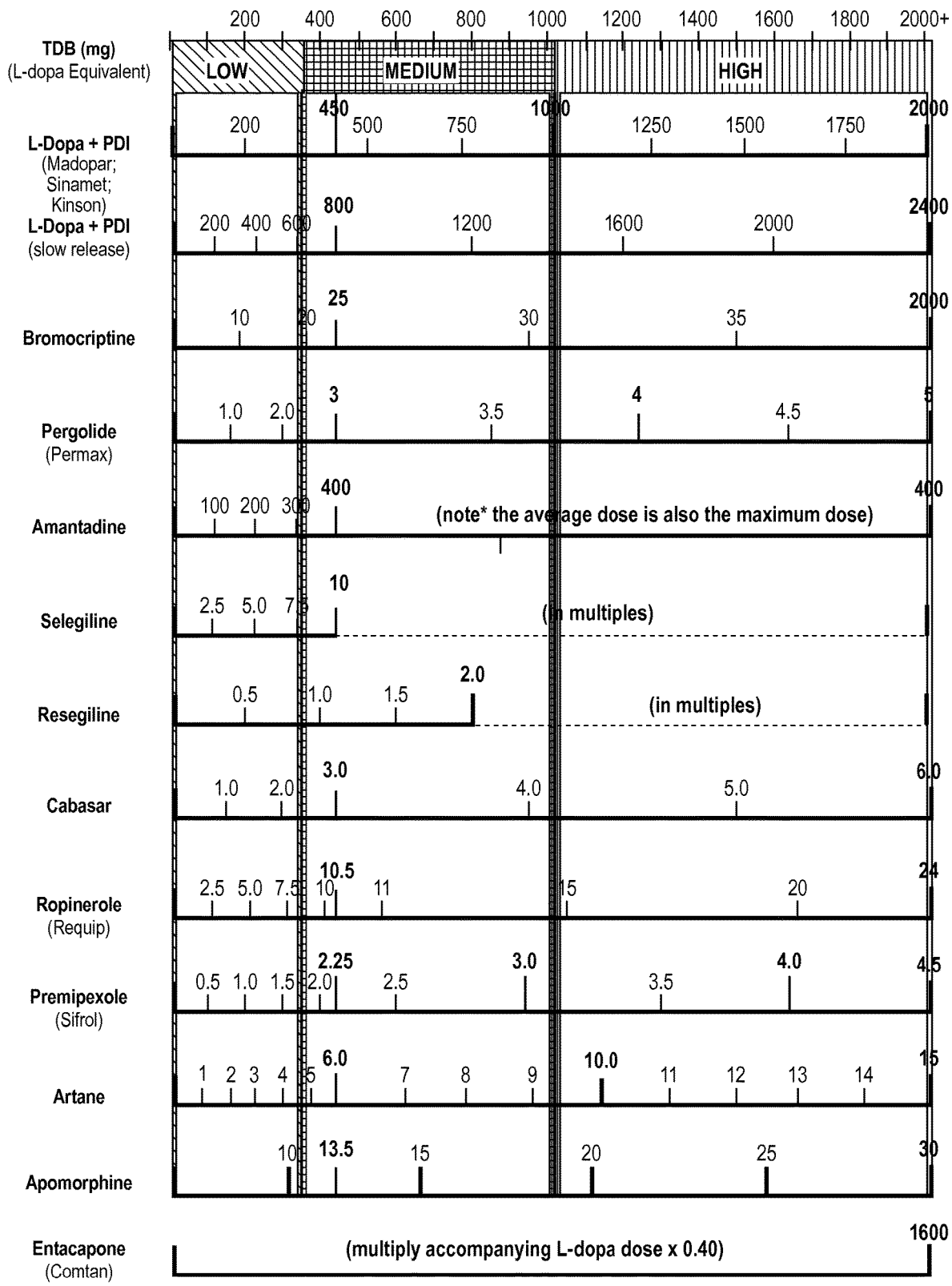

The charts of FIGS. 7-15 depict the effects of long-term light therapy on the symptoms of subjects who suffer from motor-related neurological conditions—specifically demonstrating that when light therapy and drug therapy are combined, the progression of degenerative neurological diseases may be slowed or halted;

FIGS. 16 and 17 are charts showing the unfiltered spectral power distribution for a polychromatic light source and the filtered spectral power distribution for the same polychromatic light source, respectively;

FIGS. 18 and 19 are charts illustrating the effects of long-term light therapy—specifically, light predominantly including a narrow band isolated intensity of green light—on subjects who suffer from motor-related neurological conditions;

FIG. 20 is a chart that compares the average drug dosages required by subjects who suffer from motor-related neurological disorders at the outset of a prolonged light therapy study to the average drug dosages required by the subjects at the end of the prolonged light therapy study;

FIGS. 21 and 22 are charts demonstrating the utility of red light in enabling the early diagnosis of motor-related neurological conditions; and FIG. 23 is a chart depicting equivalent dosages for a variety of dopamine derivatives.

DETAILED DESCRIPTION

Ambient light provides a reference point for the manner in which light may be administered to a subject in accordance with teachings of the present invention. The phrase "ambient light" refers to an amount or level of light, such as an intensity, a photon density, or an irradiance, or energy, of light. "Ambient light" may refer to a collection of wavelengths of visible light, such as those present in so-called "white light," which is more accurately referred to as "polychromatic light," or in narrower bandwidths (e.g., colors, etc.) of light. As will become more apparent from the ensuing description, it may be beneficial in some embodiments of the present invention to expose a subject to above-ambient levels of some wavelengths of light, while limiting the subject's exposure to other wavelengths of light to below-ambient levels.

As used herein, the phrase "ambient level" may refer to an average of the level or amount of a particular bandwidth of light in ambient indoor lighting. Standard indoor lighting is generally white light, or polychromatic light, having an intensity of about 50 lux to about 500 lux. Ambient indoor lighting may comprise standard indoor fluorescent lighting or standard indoor incandescent lighting.

The "average" level or amount of light of a particular bandwidth may include an average of the level or amount of that bandwidth in ambient indoor lighting at about 50 lux and the level or amount of that bandwidth in ambient indoor lighting at about 500 lux. Levels of various bandwidths of light may be considered to be "above-ambient" when they exceed the ambient levels of the same wavelengths of light present in ambient indoor lighting. Conversely, levels of various wavelengths of light are considered to be "below-ambient" when they are less than the ambient levels of the same wavelengths of light present in the same type of ambient indoor lighting.

As a point of reference, standard incandescent indoor lighting, which has a collective ambient intensity of about 50 lux to about 500 lux, is composed primarily of amber and red wavelengths of light, with some green light, which makes up only a small portion of the spectrum output by standard incandescent indoor lighting. Standard fluorescent indoor lighting has the signature of mercury, with three peaks: a first peak in the indigo-deep blue range (435 nm-436 nm); a second peak in the green-yellow range (540 nm-560 nm); and a third peak at the red wavelength of 640 nm. The deep blue and green-yellow peaks of such light are, of course, less intense, photon-dense or luminescent, or energetic, than the collective intensity of light output by standard fluorescent indoor lighting.

At about 50 lux, standard indoor lighting (incandescent and/or fluorescent) has a collective photon density of $3.70 \times 10^{13}$ photons/cm$^2$/s and a collective irradiance of 13.2

μW/cm² (or 1.32×10⁻⁵ W/cm²). The blue-to-green (e.g., 460 nm to 570 nm, etc.) portion of the spectrum of about 50 lux standard indoor lighting has a photon density of 1.35×10¹³ photons/cm²/s and an irradiance of 5.1 μW/cm². These values, as well as the photon density and irradiance of narrower wavelength ranges in the blue-to-green in standard indoor lighting having an intensity of about 50 lux, are included in the following table:

TABLE 1

Standard Indoor Light at About 50 lux

| Color/Wavelength Range | Photon Density (photons/cm²/second) | Irradiance (μWatts/cm²) | Lux |
|---|---|---|---|
| Polychromatic (white) | $3.70 \times 10^{13}$ | 13.2 | 47 |
| Blue (460 nm to 500 nm) | $3.31 \times 10^{12}$ | 1.4 | 2 |
| Green (500 nm to 570 nm) | $1.03 \times 10^{13}$ | 3.8 | 22 |
| Blue-to-Green (460 nm to 570 nm) | $1.35 \times 10^{13}$ | 5.1 | 23 |
| 490 nm to 565 nm | $1.02 \times 10^{13}$ | 3.8 | 20 |
| 520 nm to 565 nm | $7.25 \times 10^{12}$ | 2.6 | 17 |
| 525 nm to 555 nm | $4.81 \times 10^{12}$ | 1.8 | 11 |
| 520 nm to 539 nm | $2.68 \times 10^{12}$ | 1.0 | 6 |

The amber-to-red (e.g., above 570 nm to 750 nm, etc.) portion of the spectrum of about 50 lux standard indoor lighting has an intensity of about 24 lux, a photon density of $2.04 \times 10^{13}$ photons/cm²/s and an irradiance of 6.7 μW/cm². The irradiance of amber-to-red light in standard indoor lighting at about 50 lux exceeds the irradiance of the blue-to-green "effective" spectrum of standard indoor lighting at about 50 lux.

At about 500 lux, the collective photon density of standard indoor lighting is $3.69 \times 10^{14}$ photons/cm²/s and the collective irradiance of standard indoor lighting is 133.5 μW/cm². At about 500 lux, the blue-to-green portion of the standard indoor lighting spectrum has a photon density of $1.53 \times 10^{14}$ photons/cm²/s and an irradiance of 58.4 μW/cm². These values, as well as the photon density and irradiance of narrower wavelength ranges in the blue-to-green in standard indoor lighting having an intensity of about 500 lux, are included in the following table:

TABLE 2

Standard Indoor Light at About 500 lux

| Color/Wavelength Range | Photon Density (photons/cm²/second) | Irradiance (μWatts/cm²) | Lux |
|---|---|---|---|
| Polychromatic (white) | $3.69 \times 10^{14}$ | 133.5 | 479 |
| Blue (460 nm to 500 nm) | $4.09 \times 10^{13}$ | 16.9 | 18 |
| Green (500 nm to 570 nm) | $1.14 \times 10^{14}$ | 42.0 | 238 |
| Blue-to-Green (460 nm to 570 nm) | $1.53 \times 10^{14}$ | 58.4 | 256 |
| 490 nm to 565 nm | $1.15 \times 10^{14}$ | 42.9 | 223 |
| 520 nm to 565 nm | $7.79 \times 10^{13}$ | 28.5 | 181 |
| 525 nm to 555 nm | $5.14 \times 10^{13}$ | 18.9 | 121 |
| 520 nm to 539 nm | $3.03 \times 10^{13}$ | 11.4 | 66 |

The amber-to-red portion of the spectrum of about 500 lux standard indoor lighting has an intensity of about 225 lux, a photon density of $1.85 \times 10^{14}$ photons/cm²/s and an irradiance of 60.4 μW/cm². The irradiance of amber-to-red light in standard indoor lighting at about 500 lux exceeds the irradiance of the blue-to-green "effective" spectrum of standard indoor lighting at about 500 lux.

Based on the foregoing, when "ambient" includes an average of the level of one or more bandwidths of light in polychromatic light of about 50 lux and the level of the same bandwidth(s) of light in polychromatic light of about 500 lux, the ambient levels of the bandwidths set forth in TABLES 1 and 2 may include the ambient values for standard indoor lighting identified in TABLE 3.

TABLE 3

Average Ambient Levels of Standard Indoor Light

| Color/Wavelength Range | Photon Density (photons/cm²/second) | Irradiance (μWatts/cm²) | Lux |
|---|---|---|---|
| Polychromatic (white) | $2.03 \times 10^{14}$ | 73.4 | 263 |
| Blue (460 nm to 500 nm) | $2.21 \times 10^{13}$ | 9.1 | 10 |
| Green (500 nm to 570 nm) | $6.19 \times 10^{13}$ | 22.9 | 130 |
| Blue-to-Green (460 nm to 570 nm) | $8.35 \times 10^{13}$ | 31.8 | 140 |
| 490 nm to 565 nm | $6.24 \times 10^{13}$ | 23.4 | 122 |
| 520 nm to 565 nm | $4.26 \times 10^{13}$ | 15.6 | 99 |
| 525 nm to 555 nm | $2.81 \times 10^{13}$ | 10.3 | 66 |
| 520 nm to 539 nm | $1.65 \times 10^{13}$ | 6.2 | 36 |

The amber-to-red portion of the spectrum of ambient standard indoor lighting has an intensity of about 125 lux, a photon density of $1.03 \times 10^{14}$ photons/cm²/s and an irradiance of 33.6 μW/cm². The irradiance of amber-to-red light in standard indoor lighting of average intensity exceeds the irradiance of the blue-to-green "effective" spectrum of standard indoor lighting at average intensity.

As an alternative to defining "ambient" in terms of an average, "ambient" light may include polychromatic light within a range of intensities, photon densities and/or irradiances, or energies, along with the levels of light within various bandwidths of polychromatic light within such a range. Levels of various wavelengths of light may be considered to be "above-ambient" when they exceed the same levels of the same wavelengths of light in an ambient range. Conversely, levels of various wavelengths of light may be considered to be "below-ambient" when they are less than the same levels of the same wavelengths of light present in the ambient range. For purposes of this disclosure, the low end of "ambient" levels may comprise the levels of each wavelength range present in about 50 lux polychromatic light, while the high end of "ambient" levels comprises the levels of various wavelength ranges present in about 500 lux polychromatic light. With this definition of ambient, below-ambient levels would include below-about 50 lux levels, while above-ambient levels would include above-about 500 lux levels.

A method for addressing motor-related neurological conditions in accordance with teachings of this present invention includes administering light therapy to a subject who suffers from, is believed to be suffering from, or is at risk for a motor-related neurological condition. Light therapy may be administered in a manner that stimulates a dopaminergic response by the subject, which may adjust levels of one or more monoamines (e.g., melatonin, serotonin, dopamine, etc.) in the body of the subject. The administration of light therapy may be conducted in conjunction with the administration of conventional therapies, including, but not limited to, the administration of dopamine derivatives or other drugs for addressing motor-related neurological conditions. In addition to administering light therapy, a method of the present invention may include evaluating the effect of the light therapy on the subject's symptoms, if any. In cases where light therapy addresses the subject's symptoms, any conventional therapies used in conjunction with the light therapy may be adjusted (e.g., decreased, etc.) in response to the effects of light therapy on the subject. The use of light therapy that incorporates teachings of the present invention, with or without conventional therapy for addressing motor-related neurological conditions, may stimulate a dopaminergic response by the subject's body, which, among other things, may adjust levels of one or more monoamines within the subject's body (e.g., levels of melatonin in the body of a subject relative to dopamine levels in the subject's body, including levels of melatonin and dopamine within the brain of the subject, etc.).

Ocular light therapy may include the administration of light including blue-green and/or green wavelengths of light to the subject. In some embodiments, the light that is administered to the subject includes above-ambient levels of blue-green and/or green wavelengths. Light therapy that employs ambient or below-ambient levels of blue-green and/or green wavelengths is also within the scope of the present invention.

The blue-green and/or green light that is administered to the subject may be administered as blue-green light and/or green light or other types of light (e.g., polychromatic light, etc.) that include above-ambient levels of green light or blue-green light, or light that is predominantly blue-green and/or green. Nonlimiting examples include colors of light with above-ambient levels of wavelengths that are within a wavelength range of 460 nm to 570 nm, 490 nm to 570 nm, about 520 nm to 570 nm, about 525 nm to about 555 nm, above 520 nm to less than 540 nm, or any wavelength within any of these ranges.

In some embodiments, a narrow portion of the spectrum of visible light may be administered to the subject. Without limiting the scope of the present invention, the light administered to the subject may consist essentially of (i.e., with the possible addition of colors or wavelengths of visible light directly adjacent to a blue-green and/or green band) blue-green and/or green light, or consist of blue-green and/or green light.

Other embodiments of the method include administering blue-green and/or green light to the subject as part of light that comprises a plurality of different colors, or so-called "polychromatic light." In more specific embodiments, the polychromatic light may comprise so-called "white light." In some embodiments, including those where polychromatic light that includes a peak in the blue, blue-green and/or green wavelengths is delivered to a subject's eyes, the light may be delivered at an above-ambient intensity (including an intensity of about 500 lux or more, an intensity of about 1,000 lux or more, an intensity of about 1,500 lux or more, an intensity of about 4,000 lux or more, an intensity of about 5,000 lux or more, etc.).

Administration of polychromatic light may include omission of one or more wavelengths of light or elimination of one or more wavelengths from polychromatic light before the light reaches the subject's eyes, or is administered to the subject. In some embodiments, the elimination of one or more wavelengths of light from polychromatic light, including white light, may be accomplished by filtering. Filtering may reduce one or more colors or wavelengths of light to below-ambient levels (e.g., to an intensity of about 50% or less of a combined intensity of therapeutic light, such as light having wavelengths of 460 nm to 570 nm, etc.). Alternatively, filtering may substantially remove, or even completely remove, one or more colors or wavelengths of light from the polychromatic light. Filtration of one or more wavelengths from polychromatic light may be based on any of a number of factors. One embodiment of a factor upon which filtering may be based is the undesirability of one or more wavelengths (e.g., amber, orange, red, etc.).

Examples of undesirable wavelengths of light include wavelengths or colors of light that decrease the therapeutic effects of certain wavelengths of visible light (e.g., by canceling or opposing the activating effects of the therapeutic wavelengths of visible light, etc.), wavelengths or colors of light that are known to enhance or exacerbate symptoms of one or more motor-related neurological conditions, wavelengths or colors of light that may interfere with a subject's ability to exhibit a dopaminergic response or disrupt the monoamine profile in the subject's body (e.g., the subject's brain, etc.) (e.g., the melatonin-dopamine balance in the subject's body, etc.), and even wavelengths or colors of light that provide no apparent benefit when administered to a subject who suffers from, is believed to suffer from, or is at risk for suffering from a motor-related neurological condition. It has recently been found that light with wavelengths of light that are longer than those of green light (e.g., light having wavelengths of greater than 570 nm, from greater than 570 nm to about 750 nm, amber, orange, and/or red wavelengths of light, etc.) enhance or exacerbate symptoms of motor-related neurological conditions.

The bandwidth of light that is reduced, omitted or eliminated may comprise one or more of amber light, orange light and red light, or at least one wavelength of one or more the foregoing may be omitted or filtered. In more particular embodiments, visible light having wavelengths of greater than 570 nm, visible light having wavelengths of greater than 570 nm to about 750 nm, etc., may be filtered from polychromatic light prior to its administration to a subject. In a more specific embodiment, a filter may be used to reduce the amounts of visible light having wavelengths above 570 nm to below-ambient levels. In some embodiments, when ambient or below-ambient levels of blue-green and/or green light are administered to a subject, the levels of blue-green and/or green light may exceed the levels of amber, orange and/or red wavelengths of light administered (e.g., exceed a 1:1 ratio, by a ratio of about 2:1 or more, etc.). A filter that reduces wavelengths above 570 nm to below-ambient levels may allow ambient or above-ambient amounts of light of one or more wavelengths from 520 nm to 570 nm to pass therethrough. In some embodiments, visible light having wavelengths below 520 nm may also be filtered, and may restrict ocular light therapy to ambient or above-ambient amounts of one or more wavelengths of 520 nm to 570 nm.

The administration of light therapy to a subject in accordance with teachings of the present invention may be effected at one or more times during the day. In some embodiments, the light therapy may be administered at the same time or times, or substantially the same time or times, each day. The time or times of day at which light therapy is provided may be regulated, as may the intensity (e.g., photon density, etc.) of one or more wavelengths of light administered to the subject.

Light therapy may be administered to the subject in accordance with an optimal dosing schedule. The optimal dosing schedule may, in some embodiments, include light therapy once a day. In some embodiments, the optimal dosing schedule for light therapy may include administering the light therapy in the evening (e.g., at a time of day when melatonin levels are typically increasing, etc.). In a specific, but nonlimiting, embodiment, the optimal dosing schedule may include administration of light therapy an hour-and-a-half or more after the final administration of drugs to the subject during the day. In a more specific embodiment, light therapy may be administered between about 5:00 p.m. and about 3:00 a.m. or, even more specifically, between about 7:00 p.m. and about 10:00 p.m. The intensity (e.g., a photon density of about $10^{13}$ photons/cm$^2$/s to about $10^{16}$ photons/cm$^2$/s, etc.) and the duration (e.g., about one hour, about thirty minutes, etc.) of the light therapy may be tailored to reduce melatonin levels without adversely affecting the subject's sleep patterns, or circadian rhythms.

In other embodiments, light therapy may be administered at a plurality of different times throughout each day. The intensity and duration of each treatment may be tailored to provide a desired effect at a particular time during the day, with two or more of the treatments differing (e.g., in color, intensity, duration, etc.) from one another. Alternatively, all of the light therapy treatments administered during the twenty-four (24) hour day may be the same as or substantially the same as (i.e., with any variance attributable merely to unintended fluctuations in intensity, time, etc.) the other treatments administered during that day.

Light therapy in accordance with teachings of the present invention may slow or halt the progression of a motor-related neurological disorder after a few treatments, or positive results may not be seen until light therapy is administered for longer periods of time (e.g., weeks, months, etc.). In any event, light therapy may be used as a long-term (e.g., six months, years, the remainder of a subject's life, etc.) treatment.

In some embodiments, light therapy may be used alone to prevent or treat a motor-related neurological condition. Stated another way, treatment of the motor-related neurological condition may consist of light therapy.

Alternatively, light therapy may be administered in conjunction with the administration of one or more other treatments for motor-related neurological conditions. In some embodiments, these other treatments comprise traditional therapies, such as cellular therapies (e.g., with fetal cells, stem cells, etc.), surgical treatments, and the like.

In embodiments where light therapy is administered to a subject in connection with drug therapy, or pharmacological treatment, the drugs may include medications intended for treatment of motor-related neurological conditions and/or the symptoms of such conditions. Non-limiting examples of such drugs include those that target the dopamine (DA), noradrenaline (NA) and serotonin (5HT) systems, as well as other drugs identified in FIG. 21. FIG. 21 illustrates the equivalent daily dosage ranges for a variety of dopamine replacement therapies, including daily dosages of such therapies that are considered to be low (between the first two continuous vertical lines), medium (between the second and third continuous vertical lines) and high (between the third and fourth continuous vertical lines). The added use of light therapy may enable a physician to prescribe lower than normal dosages (i.e., drug dosages that are typically required when melatonin production is not regulated) of these drugs to treat the diagnosed motor-related neurological condition. For example, a dosage of a particular dopamine replacement therapy that would normally (i.e., without light therapy) be in the "high" range may, with light therapy in accordance with teachings of the present invention, be reduced to the "medium" or "low" range for the same drug, or to the "medium" or "low" range for another drug listed on the Total Drug Burden table. Similarly, the use of light therapy may enable a reduction in normally "medium" range dosages to dosages in the "low" range. Reducing the dosages of drug therapies may also reduce or eliminate the side-effects of the drugs, along with the need for additional drugs to treat any side-effects.

In some embodiments, the times at which drugs are administered in an optimal dosing schedule are distinct from the time or times of the day at which light therapy is administered. In a more specific embodiment, drug treatment in accordance with an optimal dosing schedule may occur during a first part of the day, while light therapy is administered during a second part of the day. For example, drugs may be administered during the day, while administration of light therapy occurs during the evening. In a more specific embodiment, drug administration may start sometime during the morning (e.g., about thirty minutes before a subject's symptoms would otherwise (without taking the drugs) typically appear) and be complete by 5:30 p.m., while light therapy is administered between 7:00 p.m. and 10:00 p.m.

A number of specific embodiments of dosing and treatment methods are set forth in TABLES 7-13. In those embodiments, light therapy, in the form of polychromatic light having peaks at about 435 nm to about 436 nm, about 460 nm to about 520 nm, about 540 nm to about 560 nm, and about 640 nm was administered at an intensity of about 1,000 lux to about 1,500 lux. The irradiance of the blue-green light present in the light administered to each subject was about 280 µW/cm$^2$, while the irradiance of the red light present in that light was only about 150 µW/cm$^2$. Although TABLES 7-13 provide many specifics, it should be understood that the details, particularly those concerning the use of polychromatic light (in reference to white light), its intensity, and the duration of the light therapy each day, pertain to specific embodiments of the disclosed protocols.

TABLE 4 sets forth a procedure by which light and drug (dopamine (DA) replacement, or DA agonist) therapies may be tailored for a new (de novo, or "DN") patient, who has been recently diagnosed with Parkinson's disease (PD).

TABLE 4

| Rule | Example Conditions for Photo-Pharmacological Intervention in A de novo Patient |
| --- | --- |
| DN1. Commencing Dose | In de novo patients, the commencing dose should be 50 mg of levodopa twice daily at, for example, 10:00 a.m. and 4:00 p.m. If the patient's responsiveness to levodopa diminishes over time, the dose of levodopa can be increased to 50 mg three times per day, say at the 8:00 a.m., 1:30 p.m., and 5:30 p.m. If the therapeutic effect continues to diminish during the day, each dose may be increased by increments of ¼ to ½ at each administration. |
| DN2. First Dose | If a patient experiences a symptom-free period upon wakening, the first task is to identify the time when the PD symptoms first appear. The first dose of the day should then be administered approximately 30 minutes prior to the time identified. As this may change with continued phototherapy, the time of first dose should be adjusted accordingly. |
| DN3. Last Dose | The last daily dose of DA replacement should not occur any later than 5:30 p.m. |

TABLE 4-continued

| Rule | Example Conditions for Photo-Pharmacological Intervention in A de novo Patient |
|---|---|
| DN4. Optimal Frequency and Time of Dosing | Three doses of DA replacement per day: Example times of 8:00 a.m., 1:30 p.m., and 5:30 p.m. |
| DN5. Escalation to Ceiling dose. | Total daily dosage should peak at no more than 600 mg per day in three equally divided lots. If other DA replacement drugs are taken concomitantly, they should not exceed three doses. |
| DN6. Time of Phototherapy | Exposure to light should commence between the hours of 7:00 p.m. and 10:00 p.m. Drug regimens should not be altered until an observation period of 2-4 weeks has been undertaken and the patient is in compliance. |
| DN7. Duration of Phototherapy | The duration of phototherapy should last for 1 hour and should be undertaken daily. |
| DN8. Frequency and Intensity of Emission | The frequency of emission should be polychromatic light with an intensity of about 1,000 lux to about 1,500 lux. |

In TABLE 5, a protocol for incorporating light therapy into an existing drug (pharmacological) treatment regimen is described.

TABLE 5

| Rule | Example Conditions for Photo-Pharmacological Intervention in A Patient Undergoing Pharmacological Treatment |
|---|---|
| T1. Treatment Response Stabilization (TRS) | In patients that have been maintained on DA replacement therapy for at least two years, it is first important that the patient experience some stability in their therapeutic response to their drug regimen prior to commencing added treatment with light therapy. This requires professional assessment and stabilization for a period of time from 4-8 weeks. |
| T2. First Dose | If a patient experiences a symptom-free period upon wakening, the first task is to identify the time when the PD symptoms first appear. The first dose of the day should then be administered approximately 30 minutes prior to the time identified. |
| T3. Last Dose | The last daily dose of DA replacement should not occur any later than 5:30 p.m. A patient should not be woken to take medication. If dosing occurs after 5:30 p.m. then the dose should be incrementally reduced in size until it is eliminated (e.g., by 9:00 p.m.). Substitute doses may be inserted during the light therapy phase of treatment or by increasing other existing doses increased to compensate for any missed treatment. |
| T4. Optimal Frequency and Time of Dosing | Three doses of DA replacement therapy per day: Example times of 8:00 a.m., 1:30 p.m., and 5:30 p.m.. Existing times of drug administration can be moved by half hour increments to achieve a balance between optimal therapeutic effects and minimal side effects and to approximate the optimal dosing regimen. |
| T5. Ceiling dose | Patients on doses larger than 600 mg of DA replacement therapy per day in three equally divided lots can incrementally reduce their total dose of DA replacement therapy by ¼ to ½ dose increments while balancing therapeutic effects and adverse effects. |
| T6. Time of Phototherapy | Exposure to light should commence between the hours of 7:00 p.m. and 10:00 p.m. Drug regimens should not be altered until an observation period of 2-4 weeks has been undertaken and the patient is in compliance. |
| T7. Duration of Phototherapy | The duration of phototherapy should last for 1 hour and should be undertaken daily. |
| T8. Frequency and Intensity of Emission | The frequency of emission should be polychromatic light with an intensity of about 1,000 lux to about 1,500 lux. |

As is apparent from TABLE 5, in addition to therapies that include the administration of drugs in conjunction with light therapy, the present invention includes methods for reducing the dosages of drugs administered in the treatment of motor-related neurological conditions. Thus, the course of pharmacological treatment for a subject that suffers from a motor-related neurological condition may be revised to decrease the subject's dependence on one more drugs (e.g., a dopamine analog, an analog of another neurotransmitter, etc.).

A reduction in the dosage of drugs administered to a subject that suffers from a motor-related neurological condition is particularly desirable when the subject suffers from side effects of the drugs. As an example, PD patients may experience dyskinaesia, hyperkinaesia or other side effects of DA replacement therapy. These side effects are typically due to overdosing. An example of a procedure for reassessing and treating PD and these side effects with drug and light therapies is described by TABLE 6.

TABLE 6

| Rule | Example Conditions for Photo-Pharmacological Intervention in A Patient Experiencing Hyperkinaesia or Dyskinaesia after Pharmacological Treatment |
|---|---|
| D1. Treatment Response Stabilization (TRS) | In patients that have been maintained on DA replacement therapy for at least two years, it is first important that the patient experience some stability in their therapeutic response to their drug regimen prior to commencing added treatment with light therapy. This requires professional assessment and stabilization for a period of time from 4-8 weeks. |
| D2. First Dose | If a patient experiences a symptom-free period at any time during the day or night, the first task is to identify the time when the PD symptoms first appear. Doses of DA replacement the day should be administered strategically around the time identified. |
| D3. Last Dose | The last daily dose of DA replacement should not occur any later than 5:30 p.m. A patient should not be woken to take medication. If dosing occurs after 9:00 p.m. then the dose should be incrementally reduced in size until it is eliminated. Substitute doses may be inserted during the light therapy phase of treatment or by increasing other existing doses increased to compensate for any missed treatment. |
| D4. Optimal Frequency and Time of Dosing | Three doses of DA replacement therapy per day: Example times of 8:00 a.m., 1:30 p.m., and 5:30 p.m. Existing times of drug administration can be moved by half hour increments to achieve a balance between optimal therapeutic effects and minimal side effects and to approximate the optimal dosing regimen. If additional doses are required, they should be inserted at times determined after detailed monitoring of therapeutic effects versus adverse side effects. |
| D5. Ceiling Dose | Patients on doses larger than 600 mg of DA replacement therapy per day in three equally divided lots can incrementally reduce their total dose of DA replacement therapy by ¼ to ½ dose increments while balancing therapeutic effects and adverse effects. |
| D6. Time of Phototherapy | Exposure to light should commence between the hours of 7:00 p.m. and 10:00 p.m. Drug regimens should not be altered until an observation period of 2-4 weeks has been undertaken and the patient is in compliance. |
| D7. Duration of Phototherapy | The duration of phototherapy should last for 1 hour and should be undertaken daily. |
| D8. Frequency and Intensity of Emission | The frequency of emission should be polychromatic light with an intensity of about 1,000 lux to about 1,500 lux. |

TABLE 7 sets forth a protocol that may be followed under circumstances where a patient experiences secondary symptoms and side effects of DA replacement therapy, such as depression, insomnia or anxiety. The protocol set forth by TABLE 10 may also be followed to reduce the consequences of polypharmacy in a patient.

TABLE 7

| Rule | Example Conditions for Photo-Pharmacological Intervention in A Patient Experiencing Secondary Symptoms Such As Insomnia, Depression and Anxiety to Reduce Polypharmacy |
|---|---|
| PAD1. Treatment Response Stabilization (TRS) | In patients that have been maintained on DA replacement therapy, are experiencing secondary symptoms such as depression, insomnia or anxiety and are undergoing drug treatment for such conditions, it is important that their conditions and treatments be clearly identified and stable before commencing this program. |
| PAD2 Withdrawing Anxiolytic, Antidepressant and Soporific Medications | After the administration of phototherapy for at least four weeks, its effects on depression, anxiety and insomnia should be carefully assessed. If these conditions have stabilized or improved, the daily dosage of drugs administered for these conditions can be gradually reduced by ¼ to ½ increments as the antidepressant, anxiolytic or soporific effects of phototherapy take effect. Careful monitoring of affect, sleep and anxiety must be undertaken professionally |
| PAD3. Time of Phototherapy | In the first instance, exposure to light should commence between the hours of 7:00 p.m. and 10:00 p.m. Drug regimens should not be altered until an observation period of 2-4 weeks has been undertaken and the patient is in compliance. |
| PAD4. Duration of Phototherapy | The duration of phototherapy should last for 1 hour and should be undertaken daily. |
| PAD5. Frequency and Intensity of Emission | The frequency of emission should be polychromatic light with an intensity of about 1,000 lux to about 1,500 lux. |

When a patient experiences tolerance to drug therapies, a protocol such as that set forth in TABLE 8 may be followed.

TABLE 8

| Rule | Example Conditions for Photo-Pharmacological Intervention in A Patient Experiencing Tolerance to DA Replacement Therapy, Including wearing off, Freezing and Between-Dose Loss of Efficacy |
|---|---|
| T1. Treatment Response Stabilization (TRS) | In patients that have been maintained on DA replacement therapy and are experiencing secondary symptoms such as depression, insomnia or anxiety and are undergoing treatment with drugs for such conditions, it is important that their conditions and treatments be clearly identified and stable before commencing this program. |
| T2 Withdrawing Anxiolytic, Antidepressant and Soporific Medications | After the application of phototherapy for at least four weeks, the effects of phototherapy on depression, anxiety and/or insomnia should be carefully assessed. If these conditions have stabilized or improved, as the antidepressant, anxiolytic or soporific effects of phototherapy take effect, the daily doses of the administered drug can be gradually reduced by ¼ to ½ increments. Careful monitoring of affect, sleep and anxiety must be undertaken professionally. |
| T3. Time of Phototherapy | In the first instance, exposure to light should commence between the hours of 7:00 p.m. and 10:00 p.m. Drug regimens should not be altered until an observation period of 2-4 weeks has been undertaken and the patient is in compliance. |
| T4. Duration of Phototherapy | The duration of phototherapy should last for 1 hour and should be undertaken daily. |
| T6. Frequency and Intensity of Emission | The frequency of emission should be polychromatic light with an intensity of about 1,000 lux to about 1,500 lux. |

TABLE 9 provides an example of a process for assessing and treating PD over long periods of several months to years with the purpose of slowing or preventing the ongoing degenerative process so as to keep the symptoms of a PD patient from worsening.

TABLE 9

| Rule | Conditions for Long-Term Photo-Pharmacological Intervention to Prevent Progression of the Disease Process |
|---|---|
| LT1. Treatment Response Stabilization | Patients should be monitored as described above in response to their daily drug regimen for primary motor symptoms and should remain stable with as few changes to their drug regimen as possible for the duration of treatment. |
| LT2 Conditions of Treatment | Light exposure should occur daily at the time required to achieve optimal therapeutic response. The number of omissions should not exceed one every two weeks, and changes to DA replacement therapy should be avoided. If the patient must be brought back into control by use of drugs, then the dose required to do so should be titrated by ¼ to ½ doses and applied at strategic times, as defined in TABLE 7. |
| LT3. Time of Phototherapy | Exposure to light should commence between the hours of 7:00 P.M. and 10:00 pm. Drug regimens should not be altered until an observation period of 2-4 weeks has been undertaken and the patient in compliant with phototherapy and titration. |

FIGS. 1 through 4 depict the effects of combining melatonin regulation therapies, such as light therapy, with drug therapy to treat motor-related neurological conditions.

In a specific embodiment, when drug and light therapies are combined, 100 mg of L-dopa may be administered to a subject three (3) times daily, with administration of the first dose occurring approximately thirty (30) minutes prior to symptom onset, and the last dose being administered at about 5:30 p.m. When the subject suffers from PD, the subject will typically remain asymptomatic for about the same amount of time every morning after he or she wakes (e.g., about an hour, up to three (3) hours, etc.). Thus, the subject will know when symptoms will start to occur during the day and, therefore, will know when to take the first dose of L-dopa.

Depending upon the severity of symptoms experienced by a particular subject, higher dosages of L-dopa may be required. FIG. 21 depicts the standard dosages of L-dopa (and a variety of other dopamine derivatives) that are prescribed for subjects who suffer from varying degrees of Parkinson's Disease. Nevertheless, when drug and light therapy are used together in accordance with teachings of the present invention, below-standard L-dopa dosages may be administered to a subject.

Of course, the same rationale may be applied to other dopamine derivative therapies by substituting an equivalent dosage of the other dopamine derivative for 100 mg of L-dopa (see, e.g., FIG. 21, which depicts equivalent dosages for a variety of dopamine derivatives). Similar drug dosages may also be applied to other motor-related neurological conditions.

Figure 1:
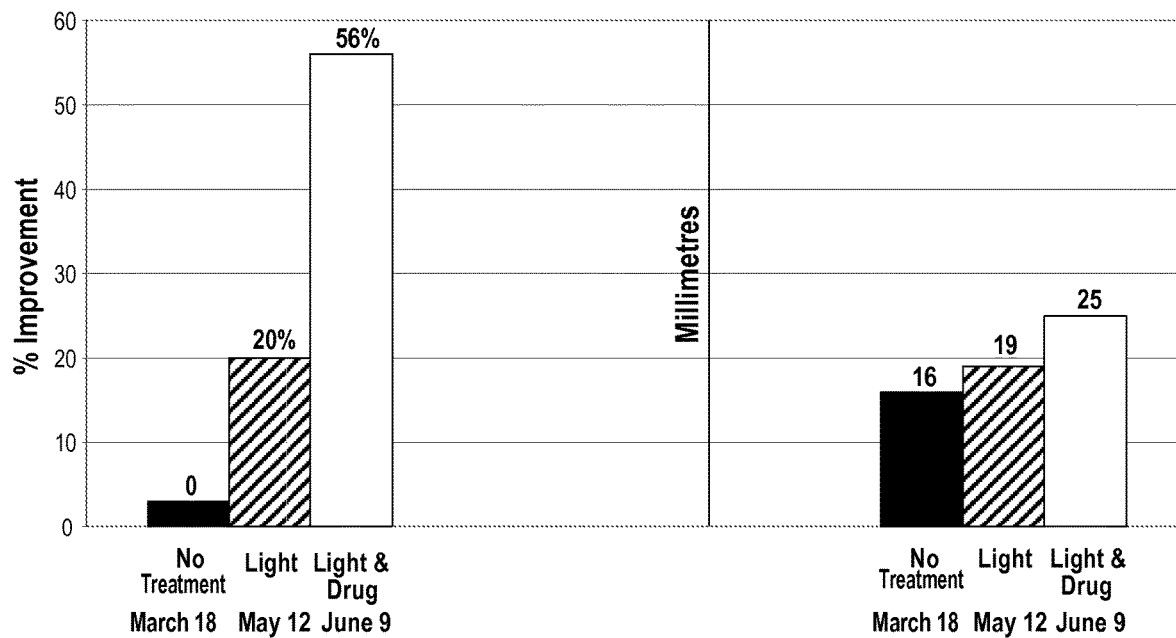
FIGS. 1-4 are charts illustrating the effects of various treatment regimens that incorporate teachings of the present invention on subjects that suffer from motor-related neurological conditions.

In the graph of FIG. 1, the effects of light therapy alone and with drug treatment on a newly diagnosed, or de novo, Parkinson's disease patient are illustrated. On the left side of the graph, the tremors experienced by the patient were evaluated. Specifically, a visual analog scale was used to quantify the patient's tremors. The tremors initially experienced by the patient (labeled "March 18") are compared with the tremors experienced by the patient after eight (8) weeks of light therapy alone (daily ocular exposure to bright white light at an intensity of about 1,000 lux to about 1,500 lux) (labeled "May 12") and the tremors experienced by the patient after another eight (8) weeks of light therapy in conjunction with drug therapy (labeled "June 9"). With light therapy alone, the patient's tremors decreased by about 20%. When light therapy was used in conjunction with drug therapy, the subject's tremors decreased by 56%.

On the right side of the graph of FIG. 1, micrographia, or a progressive decrease in the patient's handwriting, which is symptomatic of motor-related neurological conditions, such as PD, was evaluated. The diagonal distance across a routine sample of signature was measured. During the initial test, the diagonal measure of the patient's handwriting measured 16 mm. After eight (8) weeks of light therapy, the size of the patient's handwriting measured 19 mm. Eight (8) weeks after the addition of drug therapy, the diagonal measure of the patient's handwriting exhibited a further increase—to 25 mm.

The decreases in tremors and micrographia (i.e., the increase in handwriting size) demonstrate the therapeutic value of using light therapy alone or in combination with pharmacological treatment. The following results specifically illustrates that a long-term regimen of light therapy and drug treatment in accordance with teachings of the present invention can have a disease-modifying effect on (e.g., slow or halt the progression of, etc.) a degenerative neurological disease.

Figure 2A:
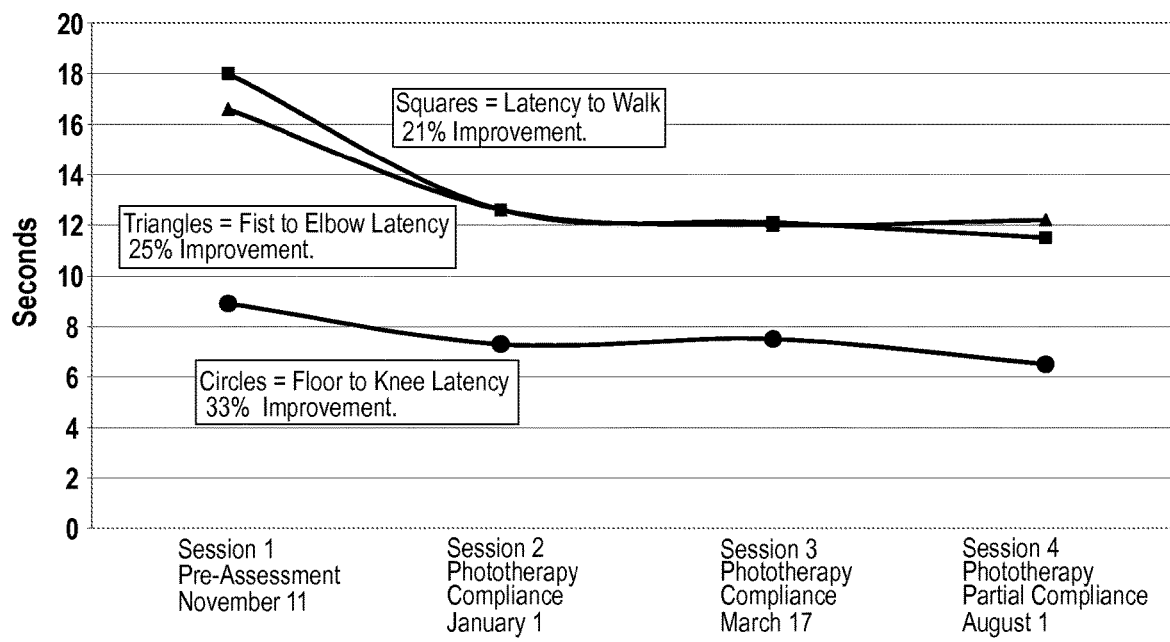
Figure 5:
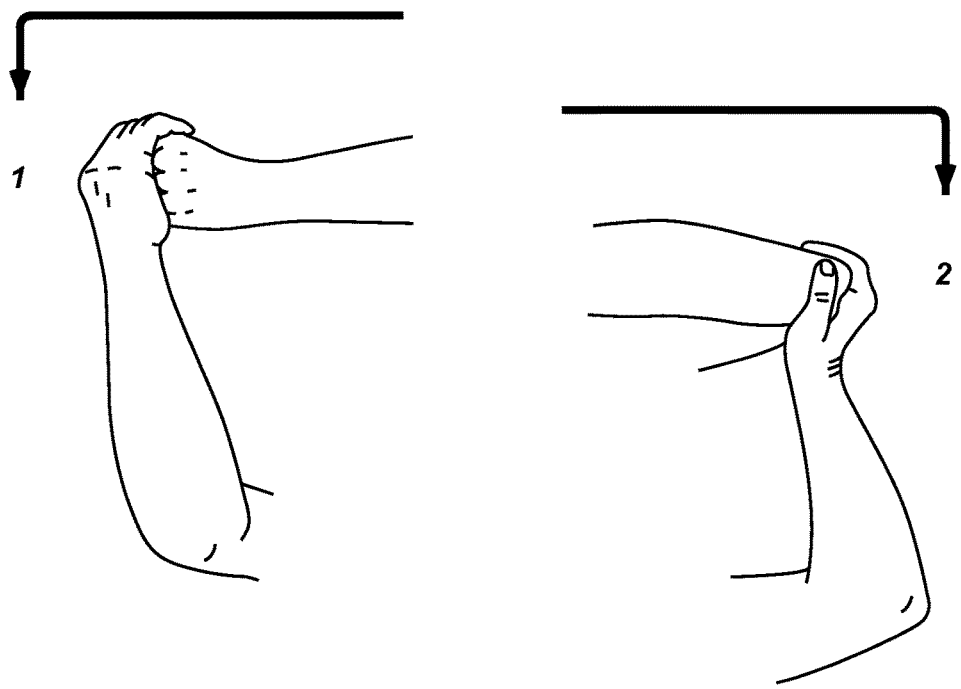
FIG. 5 illustrates the actions of a subject during a first to elbow latency test.
Figure 6:
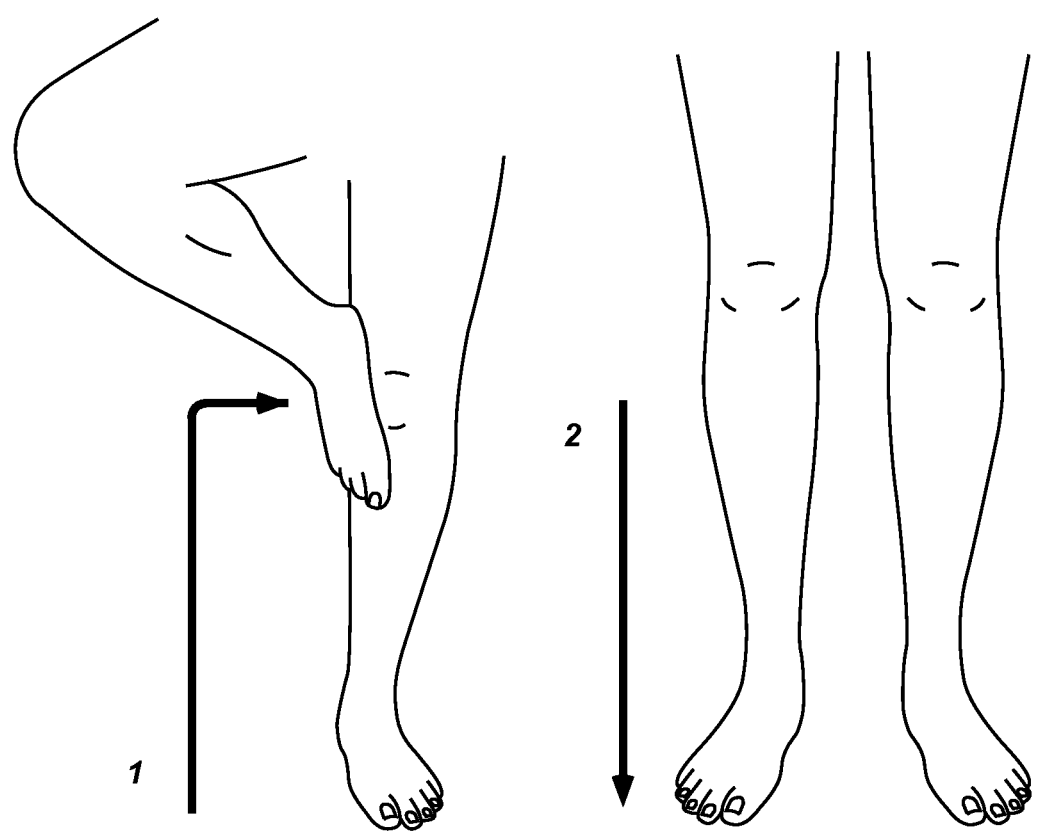
FIG. 6 illustrates the actions of a subject during a knee to floor latency test.
Figure 7:
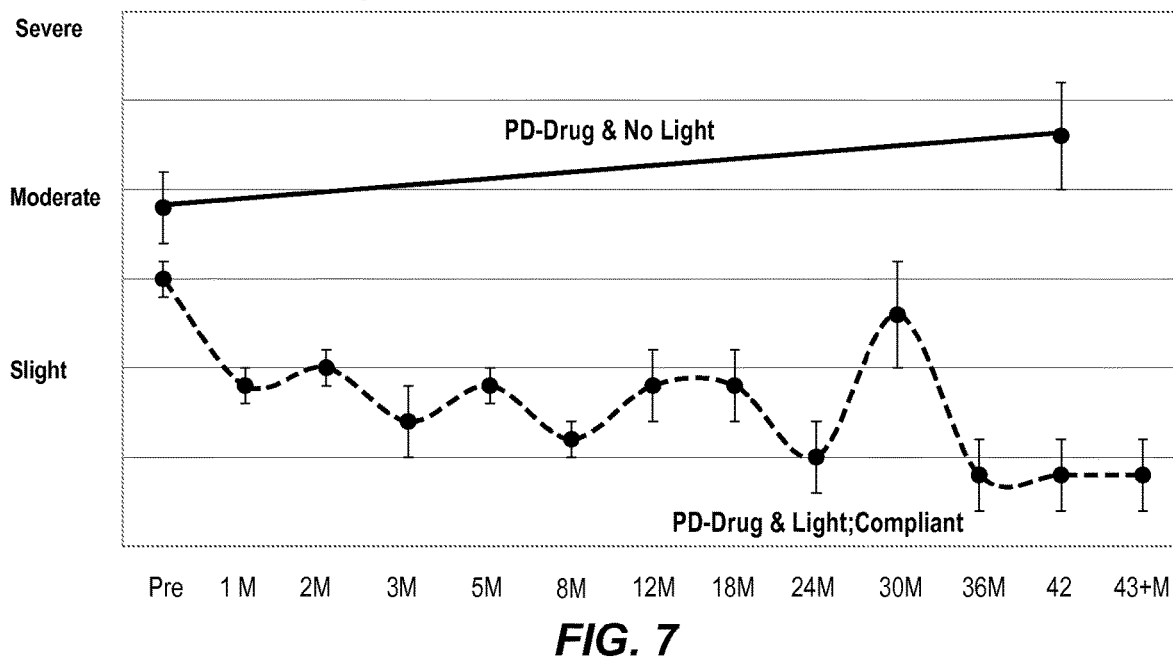
Figure 8:
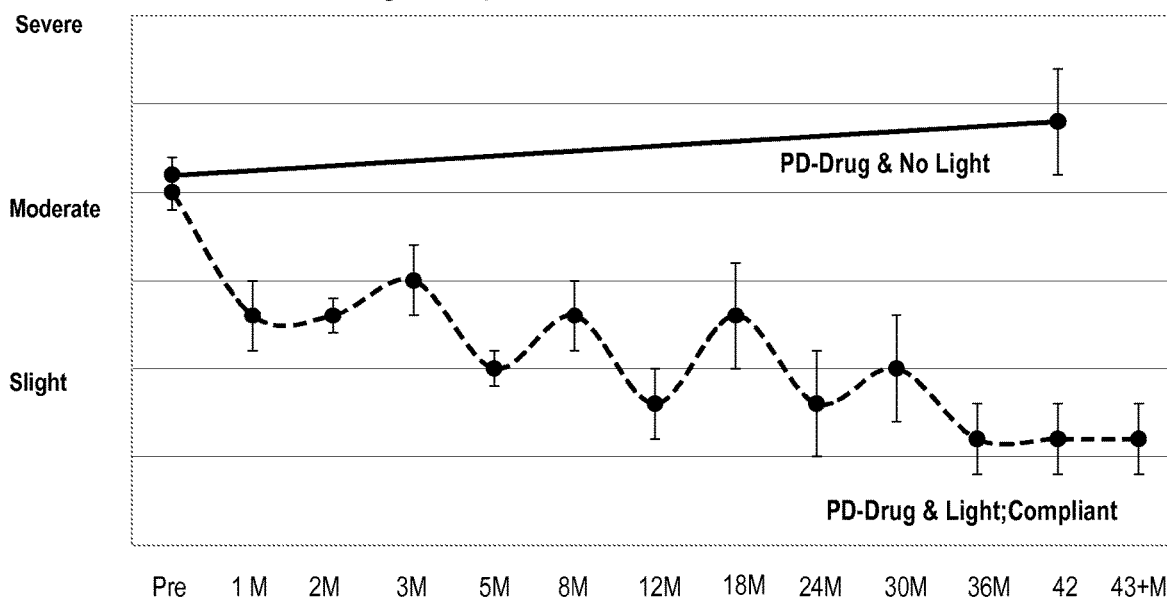
Figure 9:
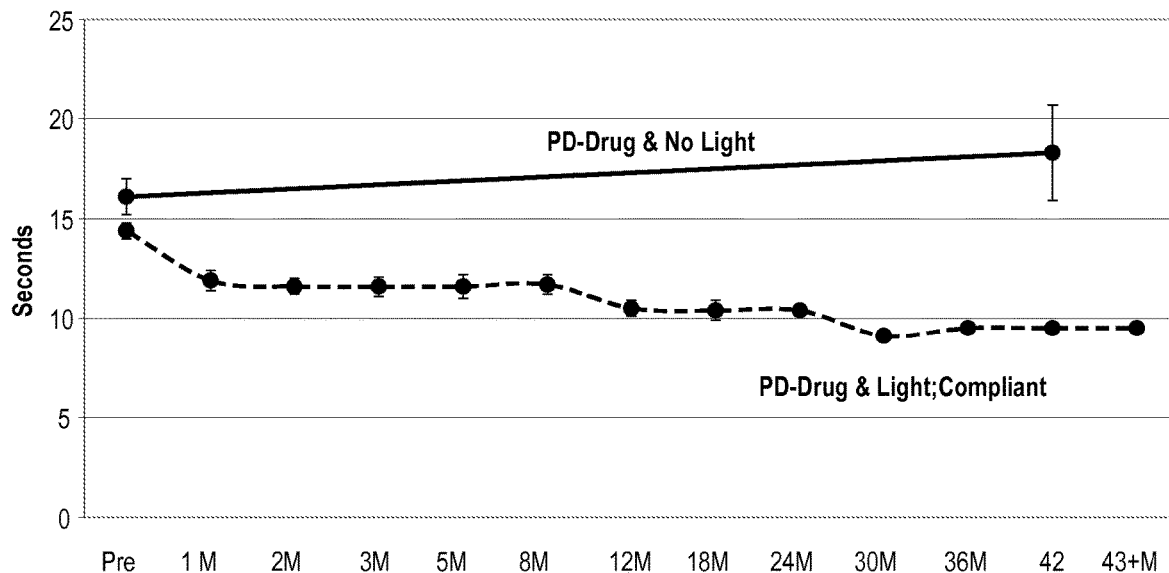
Figure 10:
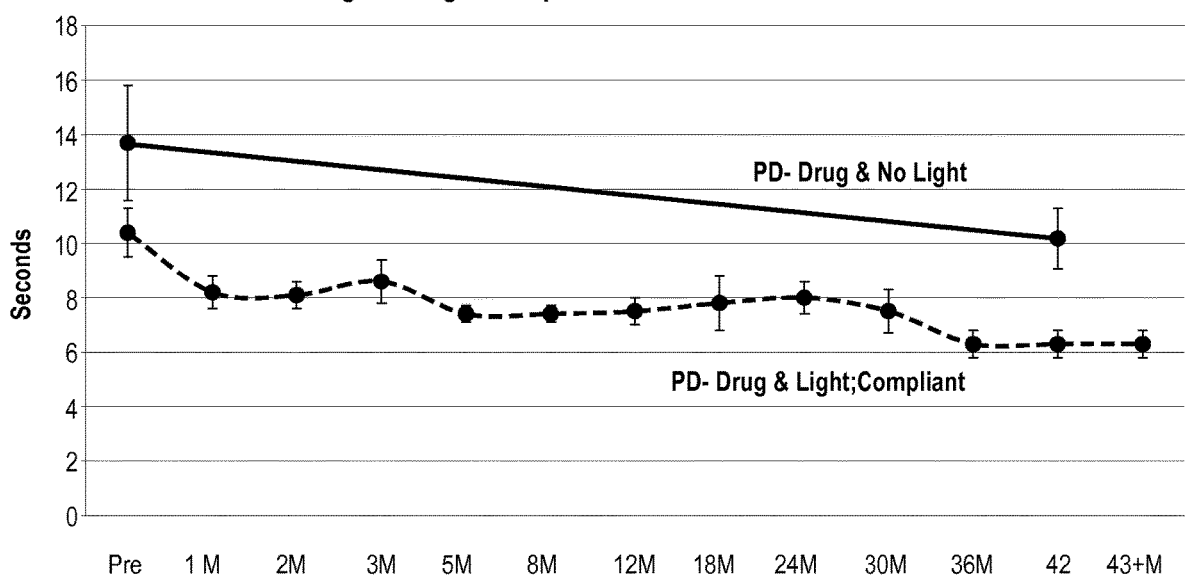
Figure 11:
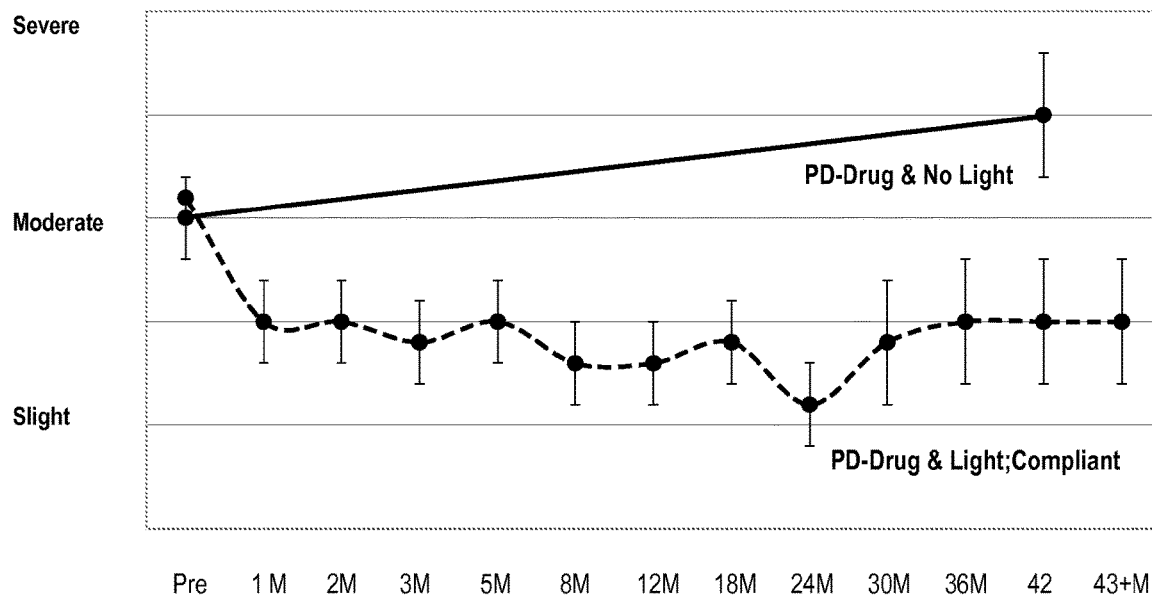
Figure 12:
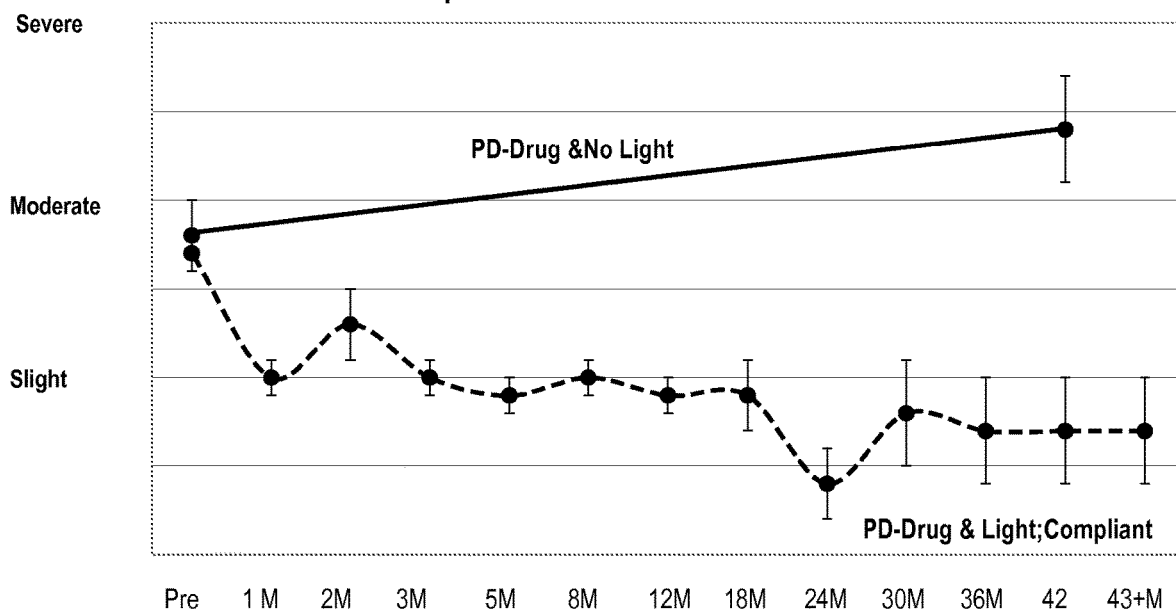
Figure 13:
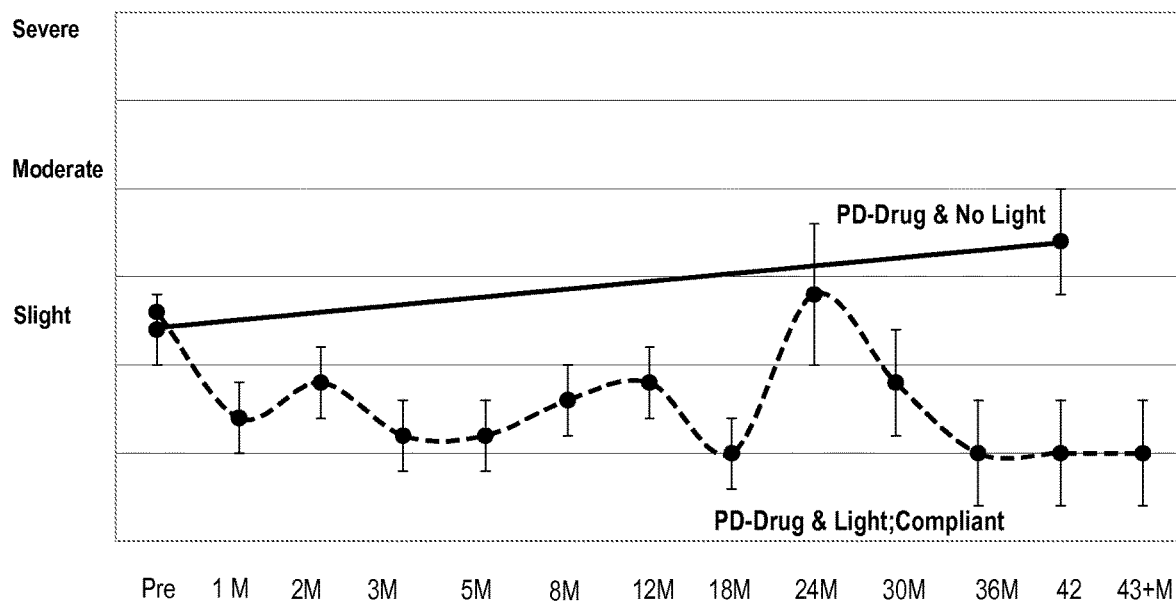
Figure 14:
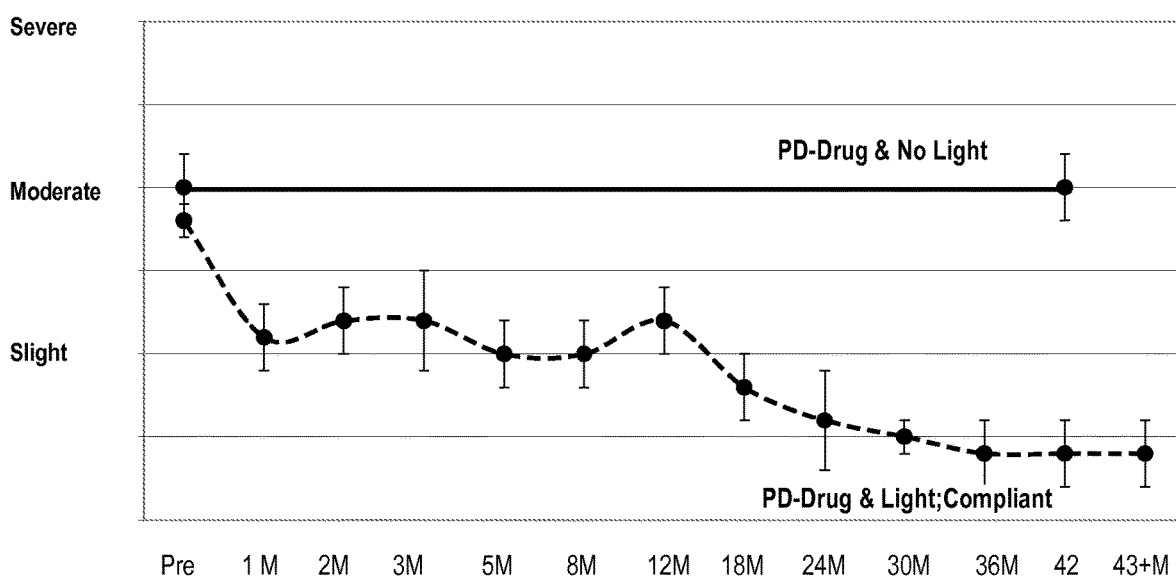
Figure 15:
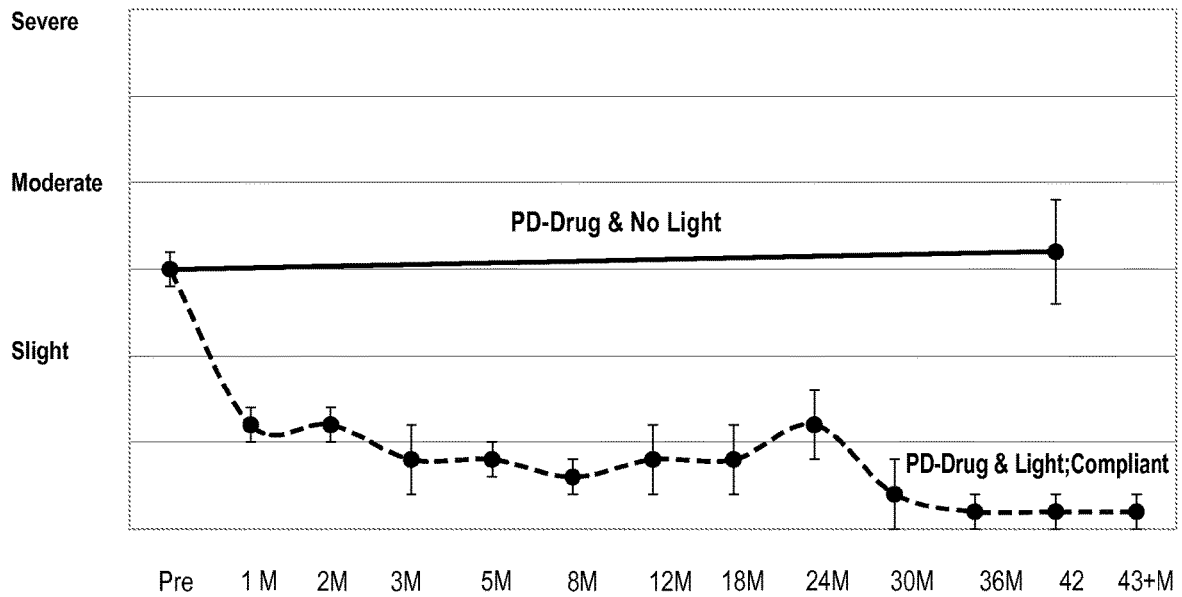

FIG. 2*a* shows the effects of light therapy on a patient who had been receiving dopamine replacement therapy (i.e., drugs) for several years. The indicators of the effectiveness of light therapy included a "latency to walk" exercise, in which the time it took the patient to walk a distance of three meters then return was measured; a "first to elbow latency" analysis was conducted, in which the time it took the patient to repeatedly move his or her hand from the first to the elbow of the patient's other, vertically oriented arm (FIG. 5) ten times was measured; and a "floor to knee latency" analysis was conducted, in which the time it took the patent to raise his or her foot from the floor to knee level (FIG. 6) ten times was measured. The results of the latency to walk tests are depicted as squares (■) in the graph of FIG. 2*a*. The results of the first to elbow latency tests appear as triangles (▲) in the graph of FIG. 2*a*. The results of the floor to knee latency analyses are depicted as circles (●) in the graph of FIG. 2*a*.

All three tests were conducted at three distinct times: (1) a pre-assessment before the initiation of light therapy; (2) a second session after the patient received daily light therapy for about seven (7) weeks; (3) a third session after the patient received daily light therapy for an additional eleven (11) weeks; and (4) a fourth session about twenty (20) weeks later, during which light therapy treatments were occasionally skipped. All three of the measures that had been evaluated exhibited improvement over the course of treatment, including striking initial rates of improvement and overall improvements of 21%, 25%, and 33% for the latency to walk, first to elbow latency, and floor to knee latency, respectively, measured in decreases in the time it took the patient to perform the prescribed exercises.

Figure 2B:
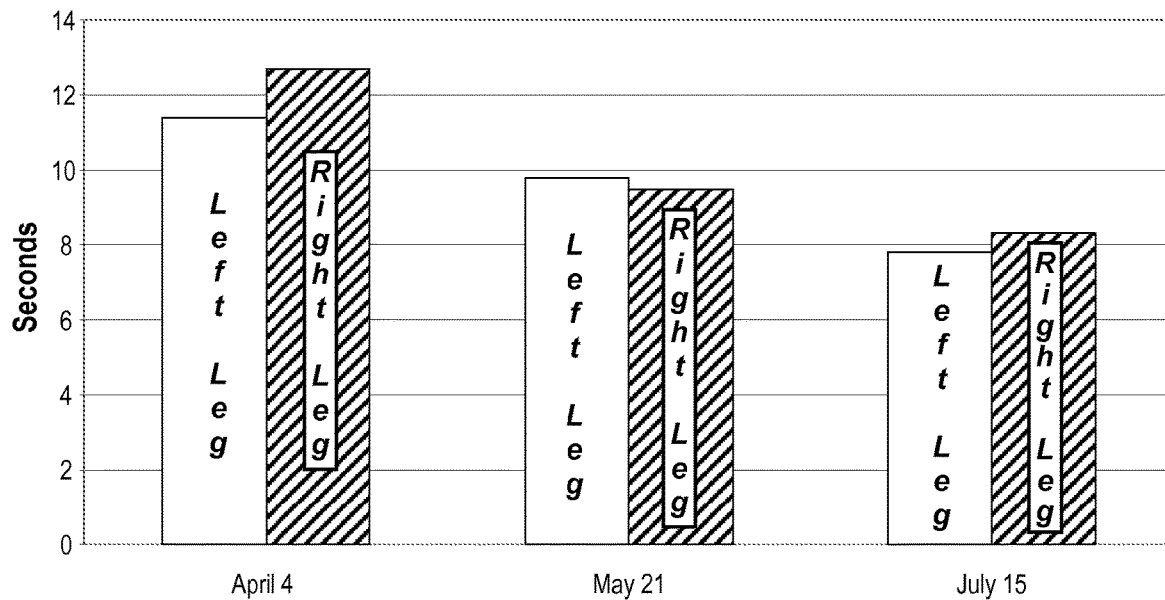

FIG. 2*b* demonstrates the improvements achieved in a patient's ability to complete the floor to knee latency exercise over the course of a regimen of light therapy administered in conjunction with previously prescribed DA replacement therapy. Again, a measured improvement of about 30%, measured in terms of a decrease in the time it took the patient to complete the exercise, was observed.

Figure 3:
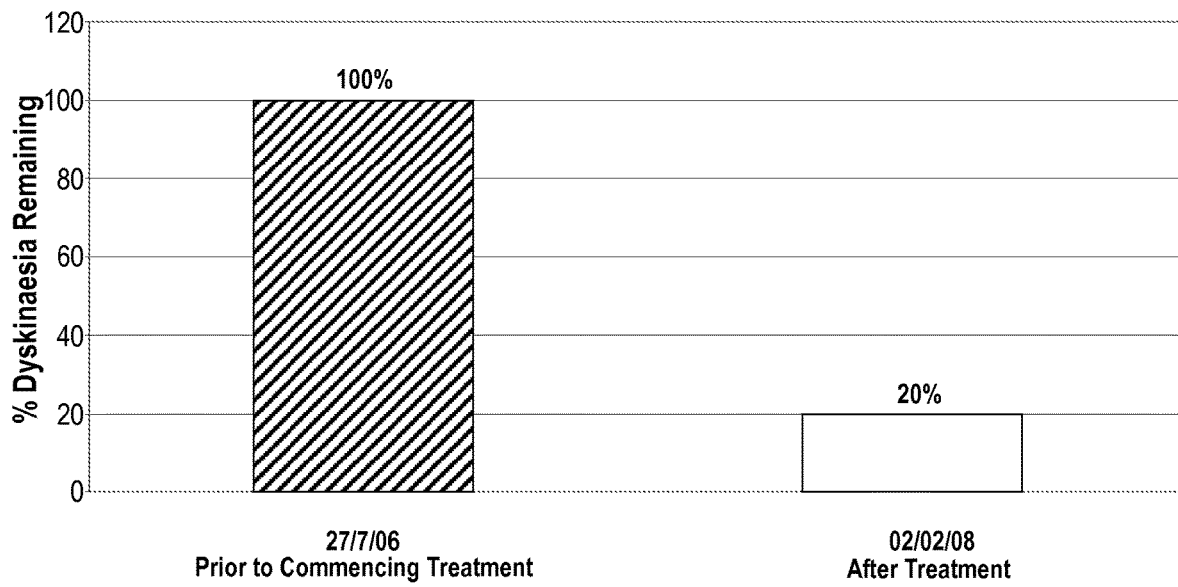

The chart of FIG. 3 shows the results of light therapy on a subject who had been receiving DA replacement therapy for a prolonged period of time, but continued to experience severe involuntary movements (dyskinesia). After about six months of light therapy, in addition to continued DA replacement therapy, the patient's dyskinesia diminished by about 80%.

Figure 4:
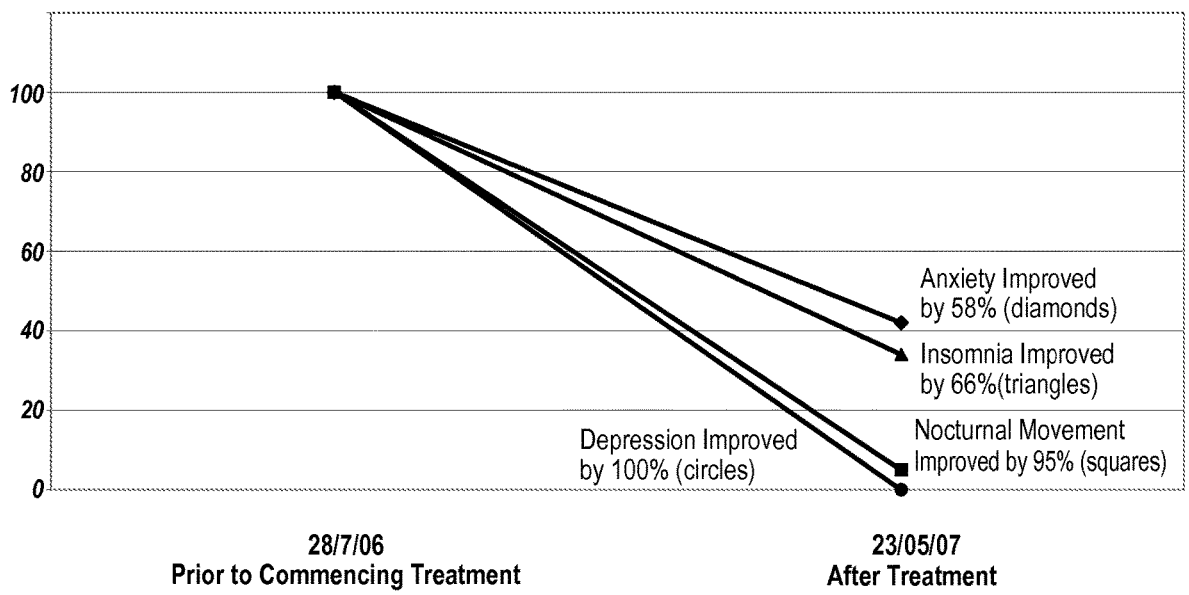

In the graph of FIG. 4, the effects of light therapy, in conjunction with continued drug (DA replacement) therapy, on various secondary symptoms of motor-related neurological conditions or side effects of DA replacement therapy. Specifically, the effects of light therapy (with continued drug therapy) on insomnia (♦), nocturnal movement (▲), depression (■), and anxiety (●) are shown. Specifically, the graph of FIG. 4 shows that the addition of light therapy to a regimen of pharmacological treatment decreased anxiety by 58%, insomnia by 66%, nocturnal movement by 95%, and depression by 100%.

In addition to the individualized results depicted by FIGS. 1-4, a larger-scale study was conducted. In that study, polychromatic light therapy was administered to subjects who were receiving drug treatment for motor-related neurological conditions. Specifically, light therapy, in the form of polychromatic light having peaks at about 435 nm to about 436 nm, about 460 nm to about 520 nm, about 540 nm to about 560 nm, and about 640 nm was administered at an intensity of about 1,000 lux to about 1,500 lux. The irradiance of the blue-green light present in the light administered to each subject was about 280 $\mu W/cm^2$, while the irradiance of the red light present in that light was only about 150 $\mu W/cm^2$.

The study, which had a duration of forty-three (43) months, involved 94 subjects. The subjects were divided into two groups: (A) thirty-one (31) Parkinson's disease patients who received standard drug therapy, but not light therapy; and (B) sixty-three (63) Parkinson's disease patients who received light therapy in addition to drug therapy, in the manner set forth in TABLE 8.

A variety of factors, including primary symptoms of Parkinson's disease and other motor-related neurological conditions (e.g., balance (FIG. 7), bradykinaesia (FIG. 8), first to elbow latency (FIG. 9), latency to walk (FIG. 10) and tremor (FIG. 11), rigidity (FIG. 12), nocturnal movement and dyskinesia (FIG. 13), etc.) and secondary symptoms of Parkinson's disease and other motor-related neurological conditions (e.g., anxiety (FIG. 14), insomnia (FIG. 15), etc.) were evaluated at the outset of the study, and at periodic intervals throughout the study. As illustrated by FIGS. 7-15, when only drug treatment was provided, all of these symptoms but latency to walk (FIG. 10) either remained the same or worsened over time. When light therapy was added to drug therapy, a significant decrease in the severity of all of the symptoms was realized (latency to walk—FIG. 10—improved at about the same rate in both groups of subjects).

In another study, the effects of yellow-green light on subjects who suffered from Parkinson's disease were evaluated. In that study, which was conducted on seven (7) subjects over an eight (8) month period of time, light therapy was administered by positioning a yellow-green filter over the light source (e.g., a filter available from LEE Filters of Hampshire, UK; a filter available from GAM Products, Inc. of Los Angeles, Calif.; a filter available from Cotech Sensitising Ltd. of Tedegra, Gwent, South Wales, UK; etc.). When a yellow-green filter is used in conjunction with a polychromatic light source such as the BRITELITE 6 energy light available from Koninklifke Philips Electronics N.V., it will filter out at least some visible light having wavelengths of more than 570 nm and at least some visible light having wavelengths that are less than 520 nm, as shown in the spectral power distribution graphs of FIG. 16 (unfiltered light) and FIG. 17 (filtered light). More specifically, FIGS. 16 and 17 show that the filter allows a peak that extends from 537 nm to 560 nm to pass, while attenuating significant amounts of light generated by the light source below 520 nm and in the range of 575 nm to 640 nm. The narrow band isolated intensity of the green light (i.e., light having one or more wavelengths of 520 nm to 570 nm) at each subject's eyes was about 880 lux, and included an above-ambient amount (an irradiance of about 130 $\mu W/cm^2$) of visible light having wavelengths of about 520 nm to 570 nm and a below-ambient amount (an irradiance of about 40 $\mu W/cm^2$) of visible light having wavelengths of more than 570 nm. As shown in FIGS. 18 and 19, the administration of light therapy in this manner resulted in gradual, consistent improvements in the primary symptoms of Parkinson's disease and many other motor-related neurological conditions, as evaluated by first to elbow latency, knee to floor latency and latency to walk tests (FIG. 18), and evaluation of each subject's arm swing, the severity of each subject's tremors and nocturnal movement by each subject (FIG. 19). Secondary symptoms of motor-related neurological conditions were also improved, as represented by the evaluation of anxiety shown in FIG. 19.

Turning now to FIG. 20, long-term light therapy has an effect on the drug dosages that are needed to address the symptoms of subjects who suffer from motor-related neurological conditions. FIG. 20 is a graph that depicts the drug dose requirements of various groups of subjects at the beginning ("Before") and end ("After") of the forty-three (43) month study.

The first (left-most) pair of bars on graph represents the drug dosages required by Parkinson's disease patients who did not receive light therapy. At the outset of the study, these subjects received, on average, 833 mg of L-dopa each day. After forty-three (43) months, the average drug dosage per-subject increased to 1142 of L-dopa each day. This represents a drug burden increase of about thirty-seven percent (37%) over forty-three (43) months. As shown in FIGS. 7-15, although drug dosages were increased over time, the symptoms of the motor-related neurological conditions suffered by these subjects actually worsened with time.

The second pair of bars represents the drug dosages administered to subjects who also received long-term periodic light therapy for their motor-related neurological conditions. On average, drug dosages were substantially constant (e.g., an increase of only about two percent (2%), etc.) over the forty-three (43) month study, with the initial average daily L-dopa dosage being about 969 mg and the final average daily L-dopa dosage being about 990 mg. Over that time, as shown in FIGS. 7-15, most of the symptoms of the motor-related neurological conditions suffered by the subjects who received light therapy improved (i.e., decreased in severity) significantly, even without any substantial increase in drug dosage.

As illustrated by the third, fourth and fifth pairs of bars in the graph of FIG. 20, the need for higher drug dosages over time decreased as the subject's compliance with prescribed light therapy regimens increased. As indicated by the fourth pair of bars, subjects who were "semi-compliant" (i.e., subjects who occasionally skipped a light therapy session or cut light therapy sessions short) initially required an average of 1056 mg of L-dopa each day and, at the end of the study, required an average of 1094 mg of L-dopa each day (a dosage increase of about three and a half percent (3½%)). Subjects who were more compliant (i.e., subjects who skipped or cut short a light therapy session less than once a week)—shown as the third pair of bars—initially required, on average, 910 mg of L-dopa per day and by the end of the study required, on average, 926 mg of L-dopa per day (a dosage increase of less than two percent (2%)). Subjects who rarely, if ever (i.e., less than once a month), skipped or cut short a light therapy session required, on average, only three (3) more milligrams of L-dopa at the end of the study (591 mg/day) than they did at the beginning of the study (588 mg/day) (about a half a percent (½%) increase).

The data provided in FIG. 20 indicate that, when light therapy is provided on a substantially regular basis to a subject who suffers from a motor-related neurological condition, the dosages of drugs administered to the subject may remain substantially the same over prolonged periods of time (e.g., a year or more, three years, four years, five years, etc.). In addition, when considered in conjunction with FIGS. 7-15, the data of FIG. 20, suggest that a combination of drug therapy and light therapy in accordance with teachings of the present invention may enable a reduction in drug dosages while preventing any increases (and, in some cases, actually decreasing) the severity of symptoms experience by a subject who suffers from a motor-related neurological condition.

These results demonstrate that the addition of light therapy in accordance with teachings of the present invention to the overall treatment regimen for subjects who are long-term sufferers of at least one motor-related neurological condition may abate symptoms of the motor-related neurological condition. This improvement in a subject's quality of life may be maintained by continuing to provide the subject with light therapy and drug therapy, with the added possibility of reduced drug dosages or reducing the rate at which drug dosages are increased over time. Combining strategic light therapy with drug therapy may also stop the progression of motor-related neurological conditions.

In addition to methods for addressing motor-related neurological conditions, the present invention includes techniques for diagnosing motor-related neurological conditions. Such a technique may include exposing a subject to certain wavelengths of light (e.g., amber, orange, red, etc.) without exposing the subject to other wavelengths of light (e.g., blue, blue-green, green, etc.). These wavelengths may temporarily inhibit dopaminergic activity. For example, melatonin production or melatonergic activity by a subject may be temporarily increased. A temporary increase in melatonergic activity may temporarily exacerbate the symptoms of a motor-related neurological condition, which may facilitate a physician's diagnosis of the motor-related neurological condition. This same phenomenon may be elicited, in some embodiments, by administering increased levels or isolated levels of amber, orange and/or red light (e.g., about the same or greater levels of amber, orange and/or red light than is present in ambient indoor light, at a greater collective intensity than blue, blue-green and/or green light, with wavelengths from 570 nm to 750 nm having a greater collective intensity than the collective intensity of wavelengths from 460 nm to 570 nm, etc.) to the subject.

In some embodiments, certain wavelengths of light may be filtered or otherwise removed from the light that is administered to a subject who is predisposed to or who may be suffering from a motor-related neurological condition.

Without limiting the scope of the present invention, wavelengths of 570 nm or less may be removed from the diagnostic light. These wavelengths may include green and/or blue-green wavelengths of light. In other embodiments, levels of administered light having wavelengths above 570 nm or levels of light having wavelengths of above 570 nm to 750 nm may exceed levels of administered light with wavelengths of 570 nm or less. In some embodiments, the subject may be exposed to one or more isolated bandwidths of amber, orange and/or red light.

In the event that physician determines that the subject is likely to suffer from a motor-related neurological condition or suffers from a motor-related neurological condition, the physician may prescribe a course of treatment for the diagnosed condition. A prescribed course of treatment may include, among other things, stimulating a dopaminergic response by the subject's body, which may adjust levels of one or more monoamines within the subject's body (e.g., one or more of the subject's melatonin, serotonin and/or dopamine levels, etc.). This may be done in any suitable manner, for example, with ocular light therapy alone or in connection with the administration of one or more drugs, and/or other suitable treatments.

One specific embodiment of a process for expediting the diagnosis of a motor-related neurological condition, such as PD, is described in TABLE 10.

have detrimental effects on patients who suffer from motor-related neurological conditions.

In a specific embodiment, a subject who is believed to be prone to a motor-related neurological condition or who may be suffering from the early stages of a motor-related neurological condition may be subjected to diagnostic therapy. Such diagnostic therapy may be affected by exposing the subject to one or more of red, orange and/or amber light. The light may be administered to the eyes of the subject. In some embodiments, repeated (e.g., daily, three times a week, etc.) administrations for prolonged periods of time (e.g., one week, two weeks, one month, etc.) may be useful in providing an accurate diagnosis.

FIG. 22 illustrates the effects of light therapy along with drug therapy to treat Parkinson's disease. A long-term coefficient ($LT_{coeff}$) was calculated using the following formula:

$$LT_{coeff} = (n_{SI}(+1) + n_{SD}(-1) + n_{SNC}(0)) / n_{SI} + n_{SD} + n_{SNC},$$

where $n_{SI}$ is the number of symptoms showing improvement, $n_{SD}$ is the number of symptoms showing deterioration, and $n_{SNC}$ is the number of symptoms showing no change. The long-term coefficient may enable a subject to better recognize his or her progression as treatment in accordance with teachings of the present invention continues over time, particularly for symptoms where improvements are very gradual, and possibly imperceptible on a day-to-day basis. In

TABLE 10

| Rule | Conditions for Early Diagnosis and Developing A Rationale for Early Treatment Thereby Preventing the Onset and Worsening of PD |
| --- | --- |
| ED1. Treatment Response Stabilization | PD Patients and undiagnosed patients should be monitored as described above in response to their daily drug regimen for primary motor symptoms and should remain stable with as few changes to their drug regimen as possible for the duration of treatment or observation |
| ED2 Conditions of Treatment | Exposure to red light should occur daily at the same time each day, usually in the evening. The number of omissions should not exceed one day every two weeks. Changes to DA replacement therapies and other medications should be avoided. |
| ED3. Time of Phototherapy | Exposure to light should commence between the hours of 7:00 p.m. and 10:00 p.m. Drug regimens should not be altered until an observation period of 2-4 weeks has been undertaken and the patient is in compliance with phototherapy and titration. The condition and well-being of the patient is monitored twice weekly during the course of treatment and terminated as soon as symptoms are manifest. |

FIG. 21 is a chart that shows the relative effects of polychromatic light and red light on the following Parkinson's disease symptoms: Agitation, anxiety, features on challenge, bradykinesia, depression, dreaming, dyskinesia, irritability, mood swing, rigidity, sleep and tremor will be exacerbated.

As shown in the left side of the chart, treatment with polychromatic light (daily treatment for one hour at an intensity of about 1,000 lux to about 1,500 lux) improved an average of sixteen (16) known PD symptoms in the treated patients, while treatment with red light yielded, on average, no improvement in PD symptoms in the treated subjects. Rather, as illustrated by the right side of the chart of FIG. 21, exposure to red light exacerbated about eleven (11) symptoms in the treated subjects, while polychromatic light only exacerbated an average of two known PD symptoms in the treated patients.

From these results, the utility of using red light (or amber and/or orange light) to enable early detection of motor-related neurological conditions is apparent. In addition, it can be seen that the red portion of polychromatic light may some embodiments, the long-term coefficient or any other means for quantifying a subject's progress may be embodied by a computerized feedback system.

Although the foregoing description contains many specifics, these should not be construed as limiting the scope of the invention or of any of the appended claims, but merely as providing information pertinent to some specific embodiments that may fall within the scopes of the invention and the appended claims. Features from different embodiments may be employed in combination. In addition, other embodiments of the invention may also be devised which lie within the scopes of the invention and the appended claims. The scope of the invention is, therefore, indicated and limited only by the appended claims and their legal equivalents. All additions, deletions and modifications to the invention, as disclosed herein, that fall within the meaning and scopes of the claims are to be embraced by the claims.

What is claimed:

1. A method for addressing a motor-related neurological condition experienced by a subject, comprising:

administering a course of ocular light therapy for the subject, including simultaneously administering, to at least one eye of the subject to reduce at least one symptom of the motor-related neurological condition:
above ambient peaks of light having intensities that exceed intensities of corresponding peaks of ambient light in at the following ranges: a first above ambient peak of light in a blue-to-blue-green range of wavelengths of about 460 nm to about 520 nm and a second above ambient peak of light in a green range of wavelengths of above 520 nm to less than 540 nm; and
below ambient or no light in a range of wavelengths of more than 570 nm to 750 nm.

2. The method of claim 1, wherein administering comprises administering the course of ocular light therapy at a different time of day than a drug therapy for the motor-related neurological condition is to be administered to the subject.

3. The method of claim 1, wherein administering comprises administering a course of ocular light therapy for the subject including a same spectral makeup of the ocular light therapy to the subject a plurality of times throughout each day.

4. The method of claim 2, wherein administering comprises administering a course of ocular light therapy for the subject including a plurality of time dependent spectral makeups of the ocular light therapy to the subj ect at a corresponding plurality of different times throughout the day, with each time dependent spectral makeup of the plurality of time dependent spectral makeups corresponding to at least one particular time during the day.

5. The method of claim 1, wherein administering comprises administering a course of ocular light therapy for the subject including ocular light therapy capable of stimulating a dopaminergic response in a brain of the subject.

6. The method of claim 1, further comprising:
diagnosing the motor-related neurological condition, including ocularly exposing the subject to an isolated bandwidth of at least one of amber, orange and red light.

7. The method of claim 6, wherein ocularly exposing enhances at least one symptom of at least one motor-related neurological condition.

8. The method of claim 6, wherein ocularly exposing comprises administering at least one wavelength of light within a range of greater than 570 nm to about 750 nm to the subject.

9. The method of claim 6, wherein diagnosing includes ocularly exposing the subject to light in which wavelengths of greater than 570 nm to 750 nm have a greater collective intensity than a collective intensity of wavelengths from 460 nm to 570 nm.

10. The method of claim 1, further comprising:
prescribing a drug therapy including a dosage of medication for treating the motor-related neurological condition; and
administering the drug therapy.

11. The method of claim 10, further comprising:
after repeatedly administering the ocular light therapy, reducing a dose of the medication administered to the subject in a revised course of treatment to treat the motor-related neurological condition.

12. The method of claim 10, wherein prescribing the course of ocular light therapy and prescribing the drug therapy comprise prescribing the light and drug therapies in accordance with a time-coordinated dosing schedule.

13. The method of claim 12, wherein prescribing the light and drug therapies in accordance with the time-coordinated dosing schedule comprises prescribing the light and drug therapies in such a way that the drug therapy is administered at a point in time from the morning to 5:30 p.m. and the ocular light therapy is administered in the evening, at a different time of day than the drug therapy.

14. The method of claim 12, wherein prescribing the light and drug therapies in accordance with the time-coordinated dosing schedule comprises administering the drug therapy before a predetermined time of day.

15. A method for addressing a motor-related neurological condition experienced by a subject, comprising:
administering a course of ocular light therapy to the subject in the evening for a duration of about thirty minutes or about one hour to reduce at least one symptom of the motor-related neurological condition, including simultaneously administering:
above ambient peaks of light having intensities that exceed intensities of corresponding peaks of ambient light in the following ranges: a first above ambient peak of light in a blue-to-blue-green range of wavelengths of about 460 nm to about 520 nm and a second above ambient peak of light in a green range of wavelengths of more than 520 nm to less than 540 nm; and
below-ambient or no light in a range of wavelengths of more than 570 nm to 750 nm.

16. The method of claim 15, wherein administering comprises administering the course of ocular light therapy at a different time of day than a drug therapy for the motor-related neurological condition is to be administered to the subject.

17. The method of claim 16, further comprising:
after repeatedly administering the course of ocular light therapy, reducing a dose of a medication administered to the subject in a revised course of treatment to treat the motor-related neurological condition.

18. The method of claim 16, wherein prescribing the course of ocular light therapy and prescribing the drug therapy comprise prescribing the course of ocular light theraby and the drug therapy in accordance with a time-coordinated dosing schedule.

19. The method of claim 18, wherein prescribing the light and drug therapies in accordance with the time-coordinated dosing schedule comprises prescribing the light and drug therapies in such a way that the drug therapy is administered at a point in time from the morning to 5:30 p.m.

20. The method of claim 18, wherein prescribing the light and drug therapies in accordance with the time-coordinated dosing schedule comprises administering the drug therapy before a predetermined time of day.

21. A method for addressing a motor-related neurological condition experienced by a subject, comprising:
administering, in the evening, a course of ocular light therapy fora duration sufficient to stimulate a dopaminergic response in the subject to reduce symptoms of the motor-related neurological condition without adversely affecting the subject's circadian rhythms, including simultaneously administering:
above ambient peaks of light having intensities that exceed intensities of corresponding peaks of ambient light in at the following ranges: a first above-ambient peak of light in a blue-to-blue-green range of wavelengths of about 460 nm to about 520 nm and a second above ambient peak of light in a green range of wavelengths of more than 520 nm to less than 540 nm; and below ambient or no light in a range of wavelengths of more than 570 nm to 750 nm.

22. The method of claim 21, wherein administering comprises administering the course of ocular light therapy at a different time of day than a drug therapy for the motor-related neurological condition is to be administered to the subject.

23. The method of claim 22, further comprising:
after repeatedly administering the ocular light therapy, reducing a dose of a medication administered to the subject in a revised course of treatment to treat the motor-related neurological condition.

24. The method of claim 22, wherein prescribing the course of ocular light therapy and prescribing the drug therapy comprise prescribing the ocular light therapy and the drug therapy in accordance with a time-coordinated dosing schedule.

25. The method of claim 24, wherein prescribing the light and drug therapies in accordance with the time-coordinated dosing schedule comprises prescribing the light and drug therapies in such a way that the drug therapy is administered at a point in time from the morning to 5:30 p.m.

26. The method of claim 24, wherein prescribing the light and drug therapies in accordance with the time-coordinated dosing schedule comprises administering the drug therapy before the evening.

27. The method of claim 15, wherein administering the course of ocular light therapy to the subject in the evening comprises administering the course of ocular light therapy between about 7:00 p.m. and about 10:00 p.m.

28. The method of claim 21, wherein administering, in the evening, the course of ocular light therapy comprises administering the course of ocular light therapy between about 7:00 p.m. and about 10:00 p.m.

29. The method of claim 1, wherein administering occurs in the evening.

30. The method of claim 1, wherein administering occurs for a duration that reduces the at least one symptom of the motor-related neurological condition without adversely affecting the subject's circadian rhythms.

31. The method of claim 30, wherein administering occurs for about one hour.

32. The method of claim 30, wherein administering occurs for about thirty minutes.

33. The method of claim 1, wherein administering reduces at least one secondary symptom of the motor-related neurological condition.

34. The method of claim 33, wherein administering reduces at least one of Alzheimer's disease, dementia, depressive pseudo dementia, hydrocephalic dementia, dementia associated with Parkinson's disease, anxiety, generalized anxiety disorder, panic disorder, agoraphobia, obsessive-compulsive disorder, post-traumatic stress disorder, acute stress disorder, depression, bipolar disorder, a personality disorder, and an insomnia disorder.

35. The method of claim 15, wherein administering occurs without adversely affecting the subject's circadian rhythms.

36. The method of claim 21, wherein administering the above-ambient peaks of light in the blue-to-blue-green range of wavelengths and the green range of wavelengths includes administering the above-ambient peaks of light at an irradiance of greater than 31.8 $\mu W/cm^2$.

37. The method of claim 21, wherein administering the above-ambient peaks of light in the blue-to-blue-green range of wavelengths and the green range of wavelengths includes administering the above-ambient peaks of light at an irradiance of greater than 58.4 $\mu W/cm^2$.

38. The method of claim 21, wherein the duration of administering, in the evening, the course of light therapy is about one hour.

39. The method of claim 21, wherein the duration of administering, in the evening, the course of light therapy is about thirty minutes.

40. The method of claim 21, wherein administering reduces secondary symptoms of the motor-related neurological condition.

41. The method of claim 40, wherein administering reduces at least one of Alzheimer's disease, dementia, depressive pseudo dementia, hydrocephailic dementia, dementia associated with Parkinson's disease, anxiety, generalized anxiety disorder, panic disorder, agoraphobia, obsessive-compulsive disorder, post-traumatic stress disorder, acute stress disorder, depression, bipolar disorder, a personality disorder, and an insomnia disorder.

* * * * *